United States Patent
Lee et al.

(10) Patent No.: US 10,526,595 B2
(45) Date of Patent: *Jan. 7, 2020

(54) SINGLE CELL MICROFLUIDIC DEVICE

(71) Applicants: The Regents of the University of California, Oakland, CA (US); Pioneer Hi-Bred International, Inc., Johnston, IA (US)

(72) Inventors: Abraham P. Lee, Irvine, CA (US); Do-Hyun Lee, Irvine, CA (US); H. Kumar Wickramasinghe, Irvine, CA (US); Yinglei Tao, Irvine, CA (US); Xuan Li, Irvine, CA (US); Yue Yun, Johnston, IA (US)

(73) Assignees: THE REGENTS OF THE UNIVERSITY OF CALIFORNIA, Oakland, CA (US); PIONEER HI-BRED INTERNATIONAL, INC., Johnston, IA (US)

(*) Notice: Subject to any disclaimer, the term of this patent is extended or adjusted under 35 U.S.C. 154(b) by 57 days.

This patent is subject to a terminal disclaimer.

(21) Appl. No.: 15/950,982

(22) Filed: Apr. 11, 2018

(65) Prior Publication Data

US 2018/0230453 A1 Aug. 16, 2018

Related U.S. Application Data

(63) Continuation of application No. PCT/US2016/056683, filed on Oct. 12, 2016, and a
(Continued)

(51) Int. Cl.
*C12N 15/10* (2006.01)
*B01L 3/00* (2006.01)
(Continued)

(52) U.S. Cl.
CPC ............ *C12N 15/1006* (2013.01); *B01L 3/00* (2013.01); *C12N 15/101* (2013.01);
(Continued)

(58) Field of Classification Search
CPC .............. C12N 15/1006; C12Q 1/6844; B01L 3/50273
See application file for complete search history.

(56) References Cited

U.S. PATENT DOCUMENTS 2,656,508 A 10/1953 Coulter
3,380,584 A 4/1968 Fulwyler
(Continued)

FOREIGN PATENT DOCUMENTS

GB 2395196 5/2004
WO WO2007120240 A2 10/2007
(Continued)

OTHER PUBLICATIONS

International Search Report for PCT Application No. PCT/US18/55722 dated Feb. 6, 2019.
(Continued)

*Primary Examiner* — Narayan K Bhat
(74) *Attorney, Agent, or Firm* — Nguyen Tarbet

(57) ABSTRACT

Methods of non-destructively obtaining the genotype of a plant cell from a plant sample are disclosed. The plant cell is isolated from a plant cell sample using an integrated microfluidic device. The integrated microfluidic device includes an individual cell trap located downstream from a microfluidic channel and, the microfluidic device is configured to trap the plant cell in the individual cell trap. mRNA is extracted from the plant cell by contacting the plant cell with an atomic force microscope (AFM) probe and by attracting mRNA from loci of interest to the probe end using a dielectrophoresis DEP force under the alternating current
(Continued)

US 10,526,595 B2

Page 2

(AC) field applied to the probe. The genotype of the plant cell is determined from cDNA obtained from the extracted mRNA. Alternatively, the mRNA is analyzed to determine gene expression patterns of the plant cell.

12 Claims, 25 Drawing Sheets

Related U.S. Application Data continuation of application No. 15/288,969, filed on Oct. 7, 2016, now Pat. No. 9,862,941.

(60) Provisional application No. 62/241,600, filed on Oct. 14, 2015, provisional application No. 62/384,628, filed on Sep. 7, 2016.

(51) Int. Cl.
*C12Q 1/6844* (2018.01)
*C12Q 1/6806* (2018.01)

(52) U.S. Cl.
CPC ......... *C12Q 1/6806* (2013.01); *C12Q 1/6844* (2013.01); *C12Q 2537/143* (2013.01); *C12Q 2565/101* (2013.01); *C12Q 2565/107* (2013.01)

(56) References Cited

U.S. PATENT DOCUMENTS

| | | | |
|---|---|---|---|
| 4,009,435 A | 2/1977 | Hogg | |
| 5,465,582 A | 11/1995 | Bliss et al. | |
| 8,263,023 B2 | 9/2012 | Le Vot et al. | |
| 8,365,311 B2 | 1/2013 | Nawarathna et al. | |
| 8,927,040 B2 | 1/2015 | Brand et al. | |
| 9,176,504 B2 | 11/2015 | Chiou et al. | |
| 9,862,941 B2 | 1/2018 | Lee et al. | |
| 2002/0182654 A1 | 12/2002 | Jing et al. | |
| 2004/0234588 A1 | 11/2004 | Lu et al. | |
| 2005/0015001 A1 | 1/2005 | Lec et al. | |
| 2005/0106064 A1 | 5/2005 | Laurell et al. | |
| 2005/0272039 A1 | 12/2005 | Yasuda | |
| 2005/0272096 A1 | 12/2005 | Clague et al. | |
| 2006/0051329 A1 | 3/2006 | Lee et al. | |
| 2006/0177815 A1 | 8/2006 | Soh et al. | |
| 2007/0264320 A1 | 11/2007 | Lee et al. | |
| 2008/0038807 A1 | 2/2008 | Pommersheim | |
| 2008/0241875 A1 | 10/2008 | Hwang et al. | |
| 2009/0042310 A1 | 2/2009 | Ward et al. | |
| 2009/0068170 A1 | 3/2009 | Weitz et al. | |
| 2009/0075390 A1 | 3/2009 | Linder et al. | |
| 2009/0286300 A1 | 11/2009 | Le Vot et al. | |
| 2009/0298191 A1 | 12/2009 | Whitesides et al. | |
| 2011/0059556 A1 | 3/2011 | Strey et al. | |
| 2011/0086352 A1 | 4/2011 | Bashir et al. | |
| 2011/0285042 A1 | 11/2011 | Viovy et al. | |
| 2012/0034155 A1 | 2/2012 | Hyde et al. | |
| 2012/0107912 A1 | 5/2012 | Hwang et al. | |
| 2012/0196288 A1 | 8/2012 | Beer | |
| 2013/0078163 A1 | 3/2013 | Chung et al. | |
| 2013/0154671 A1 | 6/2013 | Lee et al. | |
| 2013/0171628 A1 | 7/2013 | Di Carlo et al. | |
| 2013/0210649 A1 | 8/2013 | McKnight et al. | |
| 2014/0011291 A1 | 1/2014 | Patel et al. | |
| 2014/0068797 A1 | 3/2014 | Doudna et al. | |
| 2014/0076430 A1 | 3/2014 | Miller et al. | |
| 2014/0248621 A1* | 9/2014 | Collins .............. G01N 15/1031 435/6.12 |
| 2015/0018226 A1 | 1/2015 | Hansen et al. | |
| 2016/0033378 A1 | 2/2016 | Husain et al. | |
| 2016/0123858 A1 | 5/2016 | Kapur et al. | |
| 2016/0202153 A1 | 7/2016 | Gadini et al. | |
| 2017/0014449 A1 | 1/2017 | Bangera et al. | |
| 2017/0128940 A1 | 5/2017 | Amini et al. | |
| 2017/0145169 A1 | 5/2017 | Oakey et al. | |
| 2017/0183722 A1 | 6/2017 | Link | |
| 2018/0030515 A1 | 2/2018 | Regev et al. | |
| 2018/0078940 A1 | 3/2018 | Lee et al. | |

FOREIGN PATENT DOCUMENTS

| | | |
|---|---|---|
| WO | WO2015157567 A1 | 10/2015 |
| WO | WO2016040476 A1 | 3/2016 |
| WO | WO2016126871 A2 | 8/2016 |
| WO | WO2017070169 A1 | 4/2017 |

OTHER PUBLICATIONS

International Search Report and Written Opinion of the International Searching Authority for International Application No. PCT/US16/56683, dated Dec. 27, 2016, in 15 pages.

Murata et al, "Electrochemical single-cell gene-expression assay combining dielectrophorectic manipulation with secreted alkaline phosphatase reporter system", 2009, Biosensors and Bioelectronics, 25, pp. 913-919.

Stinson et al., "Genes Expressed in the Male Gametophyte of Flowering Plants and Their Isolation", 1987, Plant Physiol., 82, pp. 442-447.

International Search Report for PCT Application No. PCT/US17/55984 dated Dec. 14, 2017.

International Search Report for PCT Application No. PCT/US18/56852 dated Jan. 11, 2019.

Lin, R., et al. "High efficiency cell encapsulation utilizing novel on-demand droplet generation scheme and impedance-based detection." 14th international conference on miniaturized systems for chemistry and life sciences, ed. H. Andersson-Svahn, S. Verpoorte, J. Emineus, N. Pam me. 2010.

J. Kim, M. Chung, S. Kim, D. H. Jo, J. H. Kim, and N. L. Jeon, "Engineering of a Biomimetic Pericyte-Covered 3D Microvascular Network," Plos One, vol. 10, p. e0133880, 2015.

X. Wang, D. T. T. Phan, A. Sobrino, S. C. George, C. C. W. Hughes, and A. P. Lee, "Engineering anastomosis between living capillary networks and endothelial cell-lined microfluidic channels," Lab on a Chip, vol. 16, pp. 282-290, 2016.

Mazutis, L. et al., Lab on a Chip, vol. 9, pp. 2665-2672 (2009).

Simon, M.G. et al., Label-Free Detection of DNA Amplification in Dropletsusing Electrical Impedance, 15th International Conference on Miniaturized Systems for Chemistry and Life Sciences 2011 (MicroTAS 2011), pp. 1683-1685 (Year: 2011).

Marsh et al. Room temperature ionic liquids and their mixtures—a review. Fluid Phase Equilibria 219 (2004) 93-98.

Oh, Woon Su, "Synthesis and applications of imidazolium-based ionic liquids and their polymer derivatives" (2012). Doctoral Dissertations. 1958. http://scholarsmine.mst.edu/doctoral_dissertations/1958.

Baret et. al, "Fluorescence-activated droplet sorting (FADS): efficient microfluidic cell sorting based on enzymatic activity," Lab Chip. Jul. 7, 2009; 9(13):1850-8. doi: 10.1039/b902504a. Epub Apr. 23, 2009.

Macosko et al., "Highly Parallel Genome-wide Expression Profiling of Individual Cells Using Nanoliter, Droplets," Cell, vol. 161, No. 5, pp. 1202-1214, May 2015.

International Search Report for PCT Application No. PCT/US18/36962 dated Aug. 30, 2018.

International Search Report for PCT Application No. PCT/US18/36952 dated Sep. 18, 2018.

Inexpensive Droplet-Based Microfluidic Platform. CIDAR lab. https://www.youtube.com/watch?v=aHvfEO1h_b4.

Kamalakshakurup et al. High-efficiency single cell encapsulation and size selective capture of cells in picoliter droplets based on hydrodynamic micro-vortices. Lab Chip, 2017, 17, 4324-4333.

Brouzes, Eric, et al. "Droplet microfluidic technology for single-cell high-throughput screening." Proceedings of the National Academy of Sciences106.34 (2009): 14195-14200.

(56) References Cited

OTHER PUBLICATIONS

S. I. Rubinow and J. B. Keller, "The transverse force on a spinning sphere moving in a viscous fluid," J. Fluid Mech., vol. 11, No. 03, p. 447, Nov. 1961.

Murata et al., Electrochemical single-cell gene-expression assay combining dielectrophoretic manipulation with secreted alkaline phosphatase reporter system, 2009, Biosensors and Bioelectronics, 25, 913-919.

Stinson et al., Genes Expressed in the Male Gametophyte of Flowering Plants and Their Isolation, 1987, Plant Physiol., 83, 442-447.

International Search Report for PCT Application No. PCT/US2016/056683 dated Dec. 27, 2016.

Doria, Arlene et al., "Rapid blood plasma separation with air-liquid cavity acoustic transducers", 15th International conference on miniaturized systems for chemistry and life sciences, Oct. 2-6, 2011, pp. 1882-1884.

Lee, Abraham P. et al., "Microfluidic air-liquid cavity acoustic transducers for on-chip integration of sample preparation and sample detection", Journal of laboratory automation, Dec. 2010, vol. 15, No. 6, pp. 449-454.

International Search Report Issued for PCT Application No. PCT/US2013/042735 dated Nov. 28, 2013.

\* cited by examiner

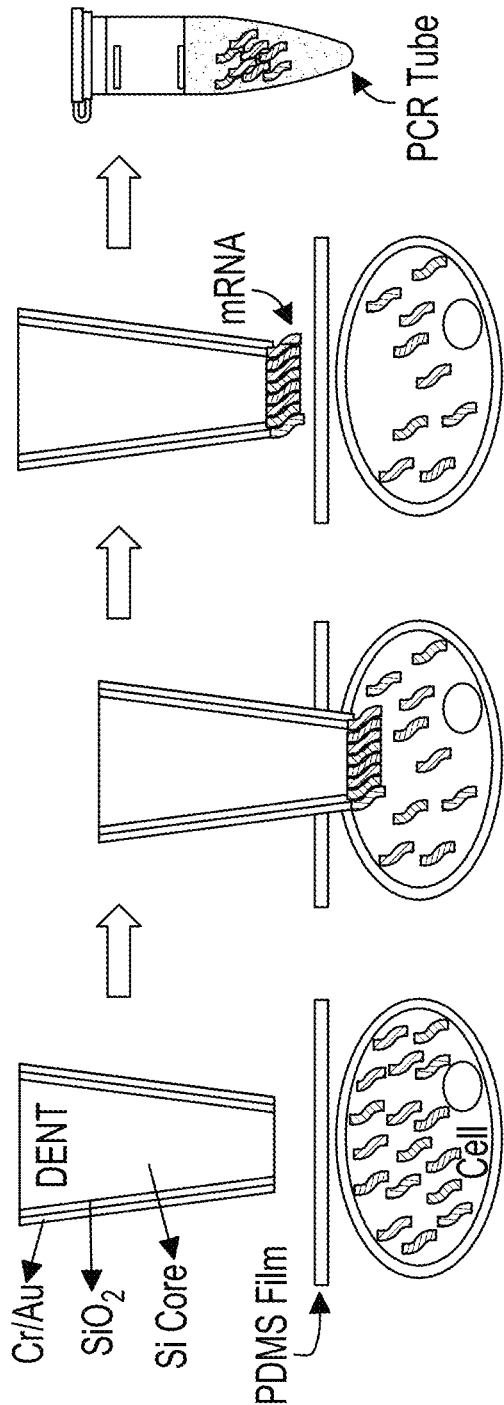
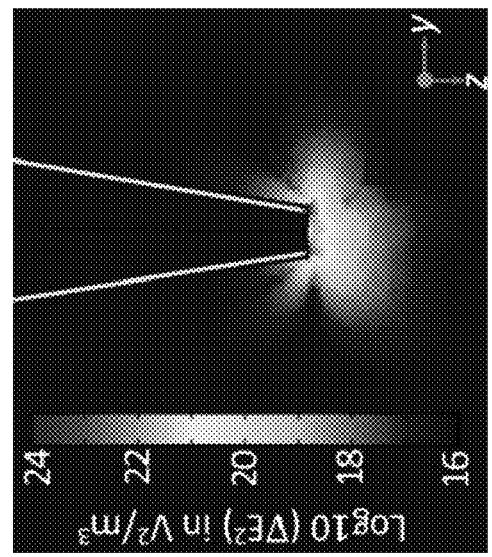
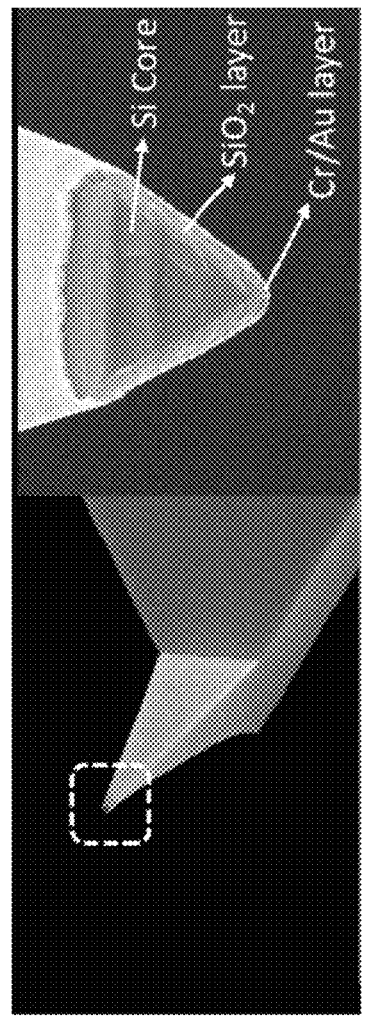
FIGURE 14(b)
FIGURE 14(c)
FIGURE 14(d)

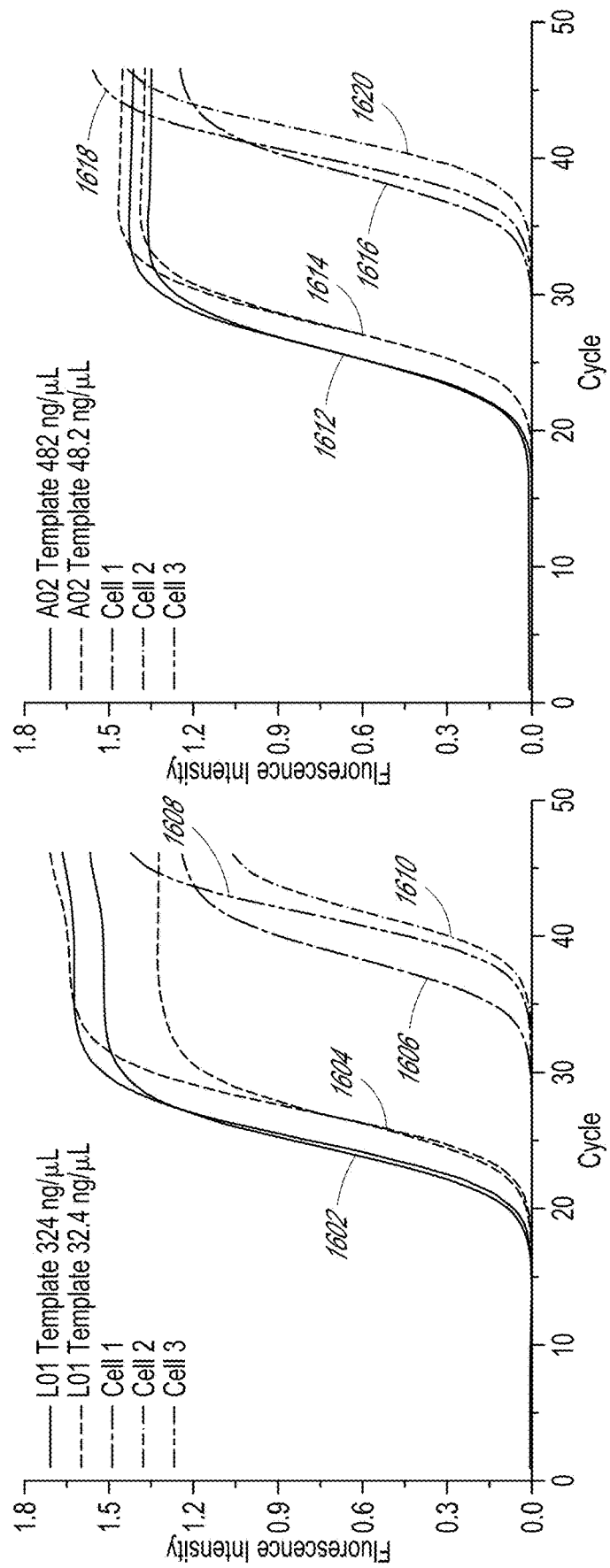

SINGLE CELL MICROFLUIDIC DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The invention relates to the use of microfluidic devices to provide the genotype and/or expression patterns of plant cells. The method may be used to non-destructively select plant cells with desired genotypes or expression patterns.

DESCRIPTION OF THE RELATED ART

The ability to detect the complexity of a biological system at single cell resolution has opened new avenues in biological and medical research in characterizing intratumor cellular heterogeneity, tracing cell lineage, measuring mutation rate, and identifying rare cell types, thereby stimulating the development of technologies that serve single cell manipulation, detection and analysis.

Single cell technologies will also provide crucial insights in plant science, such as in the understanding of key events related to plant embryo or microspore development, root and shoot differentiation, and cellular response to pathogen attack. In addition, plants possess unique single cell types, such as microspores, for which the application of single cell technologies would be particularly beneficial.

For example, not all microspores have a favorable genetic constitution; thus, it would be useful to a plant breeder to know the genotype of a microspore so that decisions can be made early on in a breeding program on whether a microspore can be used to directly or indirectly produce another plant, part thereof, or cell culture. There is a need in the art to supply single cell technologies for the purpose of obtaining the genotype of plant cells such as microspores.

SUMMARY OF EMBODIMENTS OF THE INVENTION

It would be beneficial to have micro-filtration devices that are able to isolate cells of a single size from a collection of cells of more than two sizes. Such a device would be able to isolate cells of interest from other cells that are present in a sample without having to perform complex pre-filtration procedures outside the micro-filtration devices.

This application presents embodiments of a fully integrated microfluidic platform that is capable of size-selective separation and highly efficient entrapment of single cells and in some embodiments a plurality of cells of a single size in a single device. Two different-sized microfilters are designed in sequence for removing large (in one example having a size or sizes of 25 µm or larger) and small (in one example having a size or sizes of 5 µm or smaller) particles so that continuous separation of a targeted intermediate size (in one example a size of 15 µm) population is achieved. The separated targeted microparticles can then be isolated individually by downstream trapping arrays. This straightforward approach enables efficient separation and recovery of medium-sized cells, and facilitates the individual trapping of target cells without moving parts or external forces.

In one embodiment, a device is provided for filtering solid micron scale constituents from a sample. The sample can be a biological sample. The constituents can be cells, particles or other micron scale solids. The device can include an inlet, a first filter disposed adjacent to the inlet, and a second filter disposed away from the first filter. A fluid passage is disposed between the first and second filter and provides fluid communication therebetween. A separation branch passage is provided that is in fluid communication with the fluid passage. A plurality of micron scale wells is disposed in the separation branch. The micron scale wells are configured to trap single constituents of interest.

Various embodiments of the device can further comprise a constituent concentration zone disposed in the fluid passage between the second filter and the separation branch passage, the concentration zone can be configured to concentrate the constituents toward a central portion of the fluid passage. The constituent concentration zone can include a plurality of slanted obstacles disposed in the fluid passage. In some embodiments, the slanted obstacles can comprise chevron shaped grooves. A lateral aspect of the chevron of each of the chevron shaped grooves can be closer to the micron scale wells than is the vertex of the chevron. The fluid passage can include a branched portion disposed adjacent to the first filter, the branched portion can be configured to merge at a junction between the second filter and the micron scale wells. The second filter can comprise a fan shaped filter. A source of fluid pressure can be configured to induce flow in the fluid passage in a flow direction from the second filter to the micron scale wells. The micron scale wells can have a width of about 5-15% larger than the diameter of the micron scale constituents of interest.

An embodiment of a method of isolating micron scale constituents from a sample is discussed herein. The method comprises flowing a sample including a micron scale constituents through a first filter into a fluid fluid passage. The first filter is configured to remove constituents having a width exceeding a first threshold. The method further comprises flowing an output of the first filter in a first direction through the first passage into a second filter. The second filter is configured to pass constituents having a width below a second threshold and further configured to not permit constituents of interest to pass through the second filter but to be retained between the second filter and the first filter. The method further comprises flowing the constituents of interest away from the second filter in a second direction in the fluid passage, the second direction being opposite the first direction. The method further comprises focusing the constituents of interest to a central portion of the fluid passage; and flowing the constituents of interest into a trapping zone to allow individual ones of the constituents to be isolated in the trapping zone.

Various embodiments discussed herein are directed to micro-filtration devices that are able to isolate cells of a single size from a collection of cells of more than two sizes. These devices are able to isolate cells of interest from other cells that are present in a sample without having to perform complex pre-filtration procedures outside the micro-filtration devices.

Preferred embodiments are directed to methods of non-destructively obtaining the genotype of a plant cell from a plant sample by the steps of isolating a plant cell from a plant cell sample using an integrated microfluidic device as described above. The integrated microfluidic device includes an individual cell trap located downstream from a microfluidic channel and, the microfluidic device is configured to trap the plant cell in the individual cell trap. mRNA is extracted from the plant cell by contacting the plant cell with an atomic force microscope (AFM) probe and by attracting mRNA from loci of interest to the probe end using a dielectrophoresis DEP force under the alternating current (AC) field applied to the probe. The genotype of the plant cell is determined from cDNA obtained from the extracted mRNA. Dielectrophoresis may be used to separate living plant cells from dead plant cells as part of the method. By this method, a plant cell with a desired genotype is selected and the selected plant cell is retrieved.

In preferred embodiments, the plant cell is a microspore, or protoplast.

Preferably, the plant cell sample is introduced into the integrated microfluidic device through an inlet of the integrated microfluidic device. Preferably, the introduced plant cell sample is focused towards a sidewall of the microfluidic channel. Preferably, a first constituent is separated from the focused plant cell sample. More preferably, the first constituent includes live plant cells. More preferably, separating a first constituent from the focused plant cell sample includes deflecting the first constituent of the focused plant cell sample towards a central portion of the microfluidic channel. Preferably, the method includes fluidically transporting the first constituent through the microfluidic channel to the individual cell trap.

In preferred embodiments, each plant cell is probed and the probing includes disposing the AFM probe over the plant cell trapped in the single-cell trapping array, and activating the probe to pierce a polymer membrane encapsulating the single-cell trapping array and penetrate a respective cell wall of the trapped plant cell. Preferably, the individual cell trap is part of an array of cell traps. Preferably, the external micro-manipulating instrument includes a probe tip of an atomic force microscope (AFM). Preferably, the external micro-manipulating instrument includes a dielectrophoretic nano tweezer (DENT).

In preferred embodiments, the plant cell is from maize or canola.

In preferred embodiments, the plant cell is a microspore and a microspore having a desired genotype is selected based upon a preferred genotype at least one locus, a whole genome genotype, a genome-wide genotype, at least one chromosome from a different species, a trait of interest including but not limited to simple and complex traits, a mutation, a gene knock-out, deletion, or silencing, a transgene locus, a recombinant haplotype, a genetic complement to another genotype, or any combination thereof.

In preferred embodiments, the polymer membrane has a thickness less than 5 micron and is configured to be resealable after removal of the external micro-manipulating instrument.

Embodiments of the invention are directed to method of non-destructively obtaining gene expression patterns of a plant cell by isolating an plant cell from the plant cell sample using an integrated microfluidic device. The integrated microfluidic device includes an individual cell trap located downstream from a microfluidic channel, and the microfluidic device configured to trap the plant cell in the individual cell trap. Preferably, mRNA is extracted from the plant cell by contacting the plant cell with an external micro-manipulating instrument and by attracting mRNA from loci of interest to the micro-manipulating instrument using a dielectrophoresis (DEP) force under the alternating current (AC) field applied to the micro-manipulating instrument. The mRNA is analyzed to determine gene expression patterns of the plant cell. Any method known to one of ordinary skill in the art can be used to analyze the mRNA. For example, one such method used herein is quantitative reverse transcription polymerase chain reaction (qRT-PCR).

In preferred embodiments, dielectrophoresis is used to separate living plant cells from dead plant cells as part of the method. Preferably, a plant cell with desired gene expression patterns is selected and retrieved. In preferred embodiments, the plant cell is a microspore or protoplast. In preferred embodiments, the plant cell sample is introduced into the integrated microfluidic device through an inlet of the integrated microfluidic device. Preferably, the introduced plant cell sample is focused towards a sidewall of the microfluidic channel. Preferably a first constituent is separated from the focused plant cell sample. Preferably, the first constituent includes live plant cells. Preferably, separating a first constituent from the focused plant cell sample is performed by deflecting the first constituent of the focused plant cell sample towards a central portion of the microfluidic channel. Preferably, the first constituent is fluidically transported through the microfluidic channel to the individual cell trap.

In preferred embodiments, each plant cell is probed and the probing includes disposing the external micro-manipulating instrument over the plant cell trapped in the individual cell trap and activating the external micro-manipulating instrument to pierce a polymer membrane encapsulating the individual cell trap and penetrate a respective cell wall of the trapped plant cell. In some embodiments, the individual cell trap is part of an array of cell traps. Preferably, the external micro-manipulating instrument comprises a probe tip of an atomic force microscope (AFM). Preferably, the external micro-manipulating instrument includes a dielectrophoretic nano tweezer (DENT). Preferably, the polymer membrane has a thickness less than 5 micron and is configured to be resealable after removal of the external micro-manipulating instrument.

A plant cell used in the methods herein may be from any plant including, without limitation, maize, canola, soybean, sorghum, rice, wheat, millet, alfalfa and sunflower. In some embodiments, the plant cell is from a maize or canola plant.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of the drawings.

FIG. 14B schematically illustrates a method of single-cell mRNA extraction using an external micro-manipulator, such as, for example, an atomic force microscope (AFM) probe. The illustrated method includes application of AC field between the inner Si core and outer metal layer that creates a large electric field gradient at the probe-end, generating a DEP force to attract mRNA molecules toward the probe-end. The probe is then retracted from the device, and mRNA molecules are released from the tip to perform qRT-PCR for gene expression analysis.

FIG. 14C is scanning electron microscope (SEM) image of the modified AFM probe (scale bar: 5 µm) (left panel) and a zoom-in image of the probe-end (scale bar: 200 nm) (right panel). FIG. 14D is a logarithmic scale color plot showing the simulation result (COMSOL Multiphysics) of the electric field square gradient (∇E2), once the AFM probe is inserted into the cell with an applied AC field of 1.5 Vpp, 10 MHz.

FIG. 16A illustrates gene expression analysis of Gene LO1 and FIG. 16B illustrates gene expression analysis of Gene A02 (right) using mRNA molecules extracted from single plant cells by DENT.

DETAILED DESCRIPTION

Figure 1A:
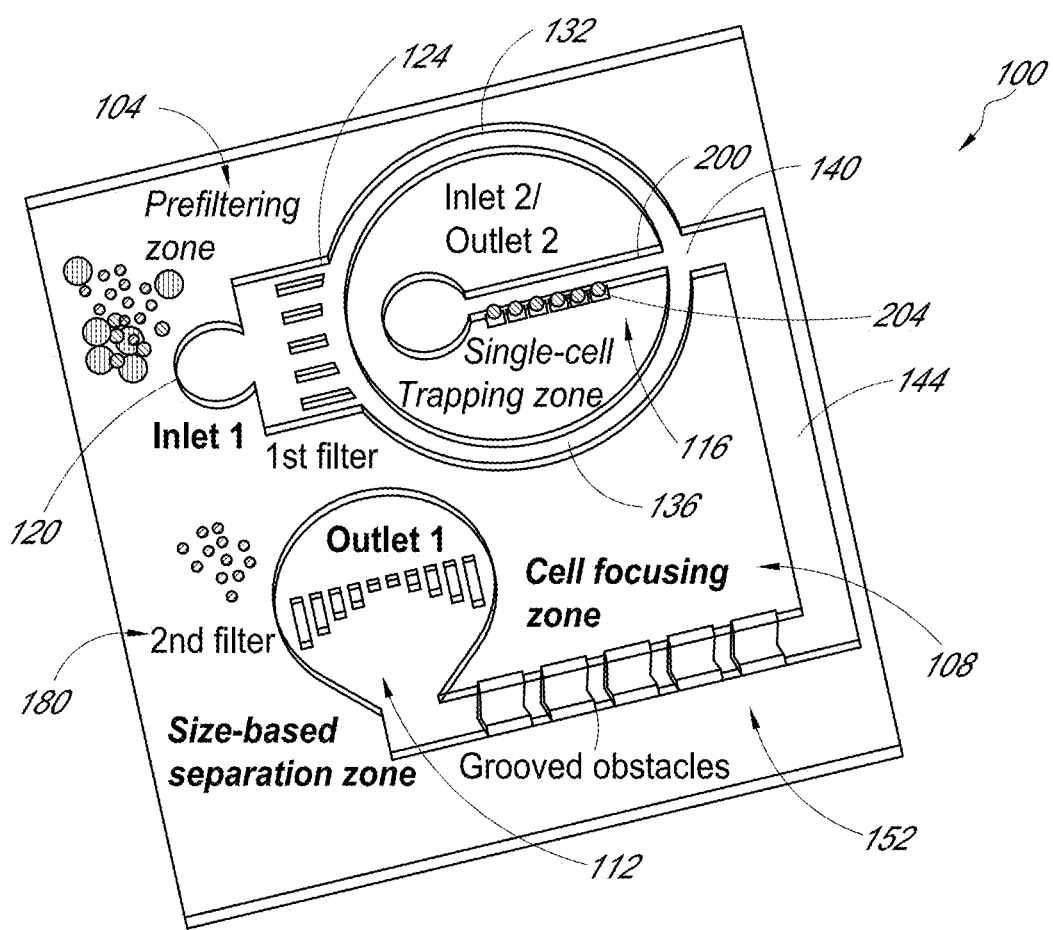
FIG. 1(a) is a schematic illustration of a micro-filtration device according to one embodiment.

It is to be understood that this invention is not limited to particular embodiments, which can, of course, vary. It is also to be understood that the terminology used herein is for the purpose of describing particular embodiments only, and is not intended to be limiting. Further, all publications referred to herein are each incorporated by reference for the purpose cited to the same extent as if each was specifically and individually indicated to be incorporated by reference herein.

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. In a claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole. The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention.

Certain definitions used in the specification and claims are provided below. In order to provide a clear and consistent understanding of the specification and claims, including the scope to be given such terms, the following definitions are provided:

An "embryo" of a plant is a young and developing plant.

"Genotype" is a description of the allelic state at one or more loci in a genome.

An "individual cell trap, without any loss of generality, is an individual cell trap which can include a groove or a concave region between two support pillars. A width of the groove or the concave region can be equal to a diameter of a cell that the cell trap is configured to capture. Each cell trap can be configured to receive input from a microfluidic delivery channel having a width wider than a width of the individual cell trap. Additionally, a rate of fluid flow in the region of the groove or the concave region can be smaller as compared to a rate of fluid flow in the delivery channel.

The terms "label" and "detectable label" refer to a molecule capable of detection. A detectable label can also include a combination of a reporter and a quencher, such as are employed in FRET probes or TAQMAN® probes. The term "reporter" refers to a substance or a portion thereof that is capable of exhibiting a detectable signal, which signal can be suppressed by a quencher. The detectable signal of the reporter is, e.g., fluorescence in the detectable range. The term "quencher" refers to a substance or portion thereof that is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state nonradiatively transfers to the quencher where it either dissipates nonradiatively or is emitted at a different emission wavelength than that of the reporter.

A "microspore" is an individual haploid structure produced from diploid sporogenous cells (microsporocyte, pollen mother cell, or meiocyte) following meiosis.

A "Microspore tetrad" as used herein is a single structure comprised of four individual, physically attached tetrad microspores.

"Non-destructive genotyping" of a plant cell, as used herein, refers to a process for determining the genotype of a plant cell in a manner that preserves the viability of the plant cell for further development. For example, for non-destructive genotyping of a microspore, the microspore may be used for development of a plant embryo or for fertilization of a female gametic cell, or may just remain viable.

As used herein, the term "plant" includes reference to whole plants, plant organs (e.g., leaves, stems, roots, etc.), seeds and plant cells and progeny of same. "Plant cell", as used herein includes, without limitation, cells from seeds, suspension cultures, embryos, meristematic regions, callus tissue, leaves, roots, shoots, gametophytes, sporophytes and pollen grains. Microspores, tetrad microspores, and protoplasts are also included in the definition of a plant cell for the methods defined herein.

A "protoplast" is the protoplasm of a living plant or bacterial cell whose cell wall has been removed.

A "tetrad" is used herein to refer to a single structure comprised of four individual tetrad microspores or four individual physically attached pollen grains.

A "tetrad microspore" as used herein is one of four microspore members belonging to a tetrad. The tetrad microspores may or may not be physically associated (i.e. enclosed within the callose wall).

This application is directed to improving particle separation technology to provide advances in biomedical engineering related technologies. Some embodiments disclosed herein provide a fully integrated microfluidic platform that is capable of size-selective separation and highly efficient entrapment of single constituents (e.g., cells or particles) in a single device.

In preferred embodiments, methods to provide the genotype of individual plant cells are provided herein. Such methods utilize a microfluidic device as described in detail below. In particular, the device as described below may be used to isolate individual plant cells from a sample and extract small molecules such as mRNA from each individual cell. The extracted mRNA is analyzed by methods such as a quantitative reverse transcription polymerase chain reaction (qRT-PCR) to determine the plant genotype. The plant cell remains viable and so then can be used for a selected purpose after determination of genotype. In preferred embodiments, the plant cell may be a microspore or a protoplast. However, any plant cell that can be isolated in a single cell form may be used in the methods described herein. Isolation of such plant cells may be accomplished by methods known in the art.

Applying selective microspores in plant breeding requires non-destructively obtaining the genotype of a microspore. In this application, methods for non-destructive genotyping a microspore are provided. The methods include obtaining genotypes in such a way such that the microspore can be later used (either directly or indirectly to develop a plant or plant part).

The methods include using an integrated microfluidic device to isolate each individual microspore from a sample preparation containing a collection of cells and tissue debris. The device enables size-specific microspore separation with defined range. The device can also separate microspores based on cell viability through dielectrophoresis (DEP) if desired. The device traps the selected microspores with high efficiency and arranges individual microspore in an isolated and encapsulated trapping array. The device can also utilize an atomic force microscope (AFM) probe to penetrate through the microspore cell wall and cell membrane and enter into the cell. The target mRNA from the loci of interest is attracted to the probe-end via the dielectrophoretic (DEP) force under the alternating current (AC) field applied by electrodes patterned on the probe. The extracted mRNA can be released for further quantitative/qualitative analysis such as, for example, qRT-PCR. The microspores remain viable after the AFM probing. The selected microspore can be retrieved for the downstream process.

The extracted mRNA may be used to generate a gene expression profile which could be based upon one or more genes in the genome. Such gene expression profiles may be obtained known techniques such as hybridization. In some embodiments, the mRNA that was extracted with the AFM probing can be reverse transcribed into cDNA. The genotype can be further inferred from the polymorphism of the cDNA and selected thereafter. One of ordinary skill in the art would understand how to obtain cDNA from mRNA and how to obtain genotypic information from cDNA using any known methods available in the art.

Also, the quantity of mRNA from cell to cell variation can also be applied as a selected trait to reflect the transcription regulation. That is, cells expressing a trait in a preferred manner, such as increased or decreased expression or timing of expression, may be preferentially selected. Finally, the AFM probes can be bound not only to mRNAs, but proteins and other small molecules. The correspondent signals all can be used as selective criterial for the breeding.

Microspore selection may be based on: at least one locus having a preferred genotype, a whole genome genotype, a genome-wide genotype, at least one chromosome from a different species, a trait of interest including but not limited to simple and complex traits, a mutation, a gene knock-out, deletion, or silencing, a transgene locus, a recombinant haplotype, a genetic complement to another genotype, or any combination thereof. One of ordinary skill in the art would be familiar with any of these features for recognizing desirable genotypes and making selections based on the genotypes.

In any of the methods described herein the plant source includes but is not limited to maize, rice, soybean, wheat, sorghum, millet, sugarcane, rye, barley, oat, canola, sunflower, cotton, soybean, or alfalfa. In preferred embodiments, the plant may be maize or canola.

FIG. 1 shows one embodiment of an integrated micro-filtration device 100. The micro-filtration device 100 includes a prefiltering zone 104, a cell focusing zone 108, a size-based separation portion 112, and a single-cell trapping zone 116. The prefiltering zone 104 is a first filter zone and the size-based separation portion 112 is a second filter zone in some embodiments.

The first filtering zone 104 includes a first inlet 120 and a first filter 124. The first filter 124 is in fluid communication with the first inlet 120. The first filter 124 is configured to prevent constituents above a size threshold from passing therethrough. The first filter 124 is configured to permit particles below the size threshold to pass therethrough. The first inlet 120 can be coupled with a sample source, e.g., a container with a fluid based biological sample. As discussed below, the plant sample can have a complex combination of solid constituent, e.g., particles or cells, dispersed within a liquid medium.

The cell focusing zone 108 is disposed downstream of the first filter 124. One or more passages provide fluid communication between the first filter 124 and the cell focusing zone 108. For example, a branched fluid passage can include a first branch 132 extending from the first filter 124 and a second branch 136 extending from the first filter 124. Each branch 132, 136 can diverge just downstream of or at the outlet of the first filter 124. Each branch 132, 136 can merge at a junction 140 disposed between the first filter and the cell focusing zone 108. A passage 144 can extend from the junction 140 to the size-based separation portion 112. The passage 144 can include one or more focusing features 152 in a portion disposed adjacent to the size-based separation portion 112. The focusing features 152 are configured to focus the flow of the constituents in the sample after the sample has been filtered in the first filter 124.

The focusing features 152 can include a series of grooved obstacles as illustrated. For example, the focusing features 152 can include a plurality of spaced apart grooves extending along the channel 144. The grooves can include chevron shaped features with lateral portions disposed upstream of a vertex located toward the center of the passage 144. The shapes has a funnel like function in which forward flowing particles disposed along the lateral walls of the passage 144 and upstream of the grooves are urged away from the lateral walls toward the center of the passage.

In some embodiments a single focusing feature 152 is provided that narrows the flow stream of the particles sufficiently for proper functioning of the device 100. In other embodiments a plurality of focusing features can be provided. Five clusters of grooves including twenty or more grooves per cluster can be provided in some embodiments. In other embodiments, the flow focusing feature 152 can include more than fifty grooves, more than 80 grooves, or 100 or more grooves. The grooves can have other features and parameters as discussed in *Field-Free, Sheathless Cell Focusing in Exponentially Expanding Hydrophoretic Channels for Microflow Cyclometry*, Cytometry Part A, 83A: 1034-1040, 2013, incorporated by reference herein in its entirety.

If the flow focusing features 152 are configured with a vertex disposed between lateral portions and the size-based separation portion 112 in the flow direction, an angle between the lateral portions and the vertex can be varied along the length of the passage 144. For example, a smaller angle can be provided for flow focusing features closer to the junction 140 and a higher angle can be provided for flow focusing features 152 closer to the toward the size-based separation portion 112.

The focusing features 152 are configured to reduce the width of the stream of particles within the passage 144. FIG. 2(f) illustrates the flow focusing ability of one embodiment. In the upper two graphs, it can be seen that a flow in the passage 144 downstream of the prefiltering zone 104 can include constituents dispersed across the width of the passage 144. The X-axis illustrates position across the width of the passage 144. At the left of the X-axis (labeled 0) is one lateral wall of the passage 144 and at the right of the x-axis (labeled 1) is the opposite lateral wall of the passage 144. In the flow being introduced into the passage 144 flowing toward the flow focusing feature 152, constituents are clustered around 0.25 and around 0.75. In the flow being introduced into the size-based separation zone 112, constituents are clustered mostly between 0.25 and 0.5 and between 0.75 and 1.0. The lower image shows that flow out of the flow focusing feature 152 is tightly clustered close to 0.5, e.g., between about 0.4 and 0.6. Thus the flow focusing feature 152 tightly clusters the constituents of interest in the passage 144.

The size-based separation portion 112 is disposed on a side of the cell focusing zone 108 opposite the junction 140 in one embodiment. The separation portion 112 is configured to separate constituents that are smaller than the size of constituents of interest from the constituents of interest. In one embodiment the separation portion 112 includes a second filter 180 with gaps or pores that are smaller than the size of the constituents of interest but larger than other constituents expected to be present in the sample. The second filter 180 can be located at an end of the passage 144.

In some embodiments, the second filter 180 is coupled with an outlet or a receptacle for collecting smaller waste constituents.

Figure 1B:
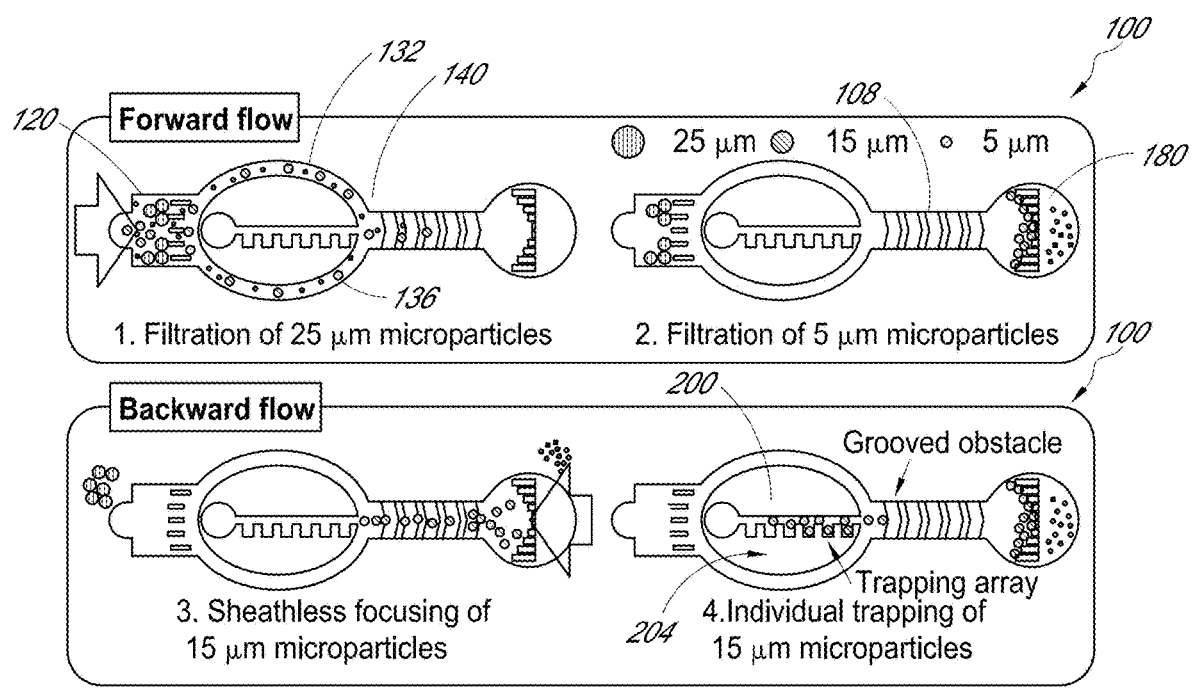
FIG. 1(b) illustrates two phases of the method of using the micro-filtration device of FIG. 1(a), in which forward flow of the sample separates or removes a particle or particles larger and smaller size than the size of the particles of interest from sample having particles of different sizes and backward flow isolates individual particles of interest from the product of the forward flow filtration.

FIG. 1(b) shows that when a sample with constituents of a variety of sizes is introduced into the inlet 120 and the fluid is caused to flow (forward) away from the inlet 120, large size particles are trapped in the first filter 124. Thus, the first filter 124 performs a pre-filtration of the sample.

The outflow of the first filter 124, which is a pre-filtered sample, flows away from the first filter 124 forward toward the second filter 180. In the illustrated embodiment, the pre-filtered sample flows through the branched passage with roughly equal volumetric flow rate in each of the two branches 132, 136. The branches 132, 136 are illustrated as conveying medium size constituents and small size constituents. The branched flow merges at the junction 140 and flows toward the second filter 180. The pre-filtered sample is further filtered at the second filter 180 such that small particles that are not desired to be trapped are removed from the pre-filtered sample. The particles of interest, in preferred embodiments, microspores, are temporarily held on the upstream side of the second filter 180. The upper right hand image in FIG. 1(b) shows the three sizes of solid constituents physically separated from each other, with the largest constituents captured in the first filter 120 and the smallest constituents passed through the second filter 180. The medium size constituents are temporarily held on the side of the second filter coupled with the passage 180.

With the small constituents excluded, the sample has been fully filtered. At this point, the flow of the filtered samples can be reversed to provide backward flow. The filtered sample flows away from the second filter 180 toward the cell focusing zone 108. The cell focusing zone causes the stream of constituents of interest to be narrowed as discussed above. The narrowed stream reduces the number of constituents in a single cross-section of the passage 144. In some embodiments the cell focusing zone 108 provides an arrangement of constituents of interest that approaches ore achieves a column of constituents that is 3-6 particles in width, and could be as narrow as a single file line in some configurations.

Further backward flow of the filtered sample causes the constituents of interest to flow into the single cell trapping zone 112. In the illustrated embodiment, the single cell trapping zone 112 includes a branch passage 200 that branches from the junction 140. The branch passage 200 includes an inlet at the junction 140 and an outlet disposed at an end thereof opposite the inlet. The inlet to the branch passage 200 is centered on a projection of the center of the passage 144 at the junction 140. As a result, constituents disposed at the center of the passage 144 that are flowing toward the inlet of the branch passage 200 tend to enter the branch passage. Fluid disposed at lateral edges of the passage 144 and stray constituents that are not particles constituents of interest are carried into the branch passages 132, 136 and away from the branch passage 200. The branch passage 200 includes one or a plurality of trapping wells 204 disposed along the branch passage 200. As the line of constituents of interest flows in the branch passage 200 from the junction 140 to the outlet, the particles are trapped in the wells 204. This allows the constituent to be further analyzed to determine properties of the constituents. Such properties can include one or more of the cell signal transduction properties, which can be further evaluated by stimulating the cells with a dynamic input signal (e.g., oscillatory chemical signals). Also, by applying physical contact directly to the cells, we can measure the mechanical response quantitatively, or, extract the intracellular products individually.

Example Embodiment to Perform Size-Based Filtration

Figure 4A:
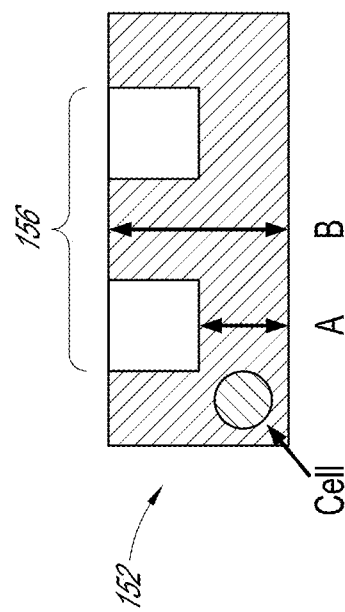
FIG. 4(a) illustrates that in certain embodiments ridges are provided in the flow focusing feature that have alternating heights.
Figure 4:
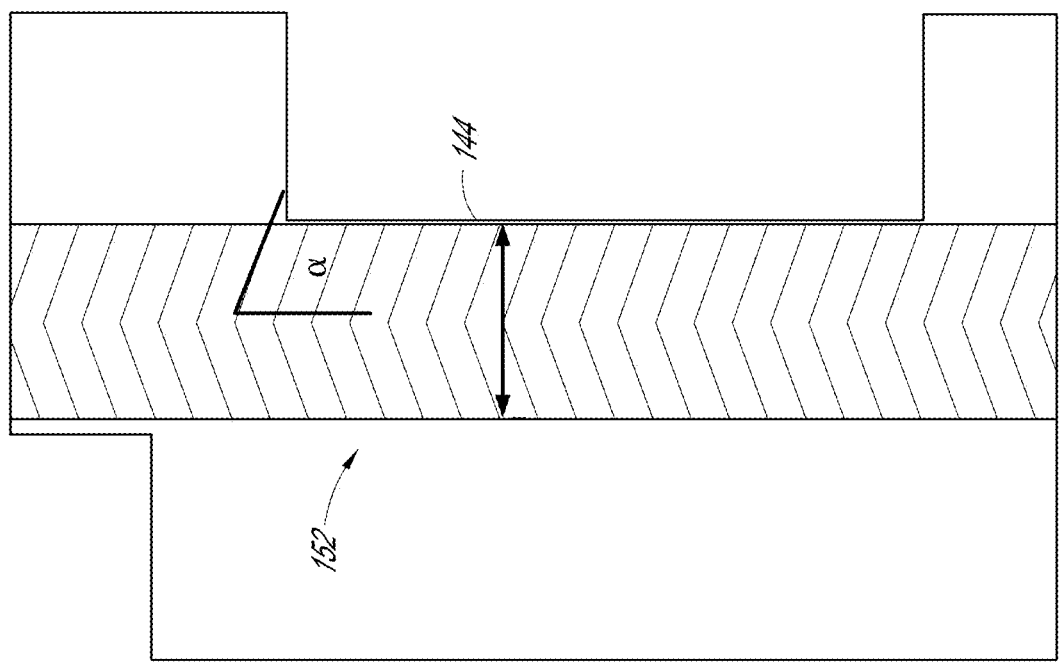
FIG. 4 illustrates further aspects of an embodiment of a flow focusing feature in a sample flow passage.

In one experiment, sized-based filtration was validated using an embodiment of the device 100 through separation of a mixture of different-sized (25, 15, and 5-μm-diameter) microparticles by the hydrodynamic filtration with two different-sized microfilters. In the embodiment of the device 100 that was tested, the filter 120 had a channel cross-section of 18×25 μm$^2$ and the filter 180 had a cross-section of 7×16 μm$^2$. For the collection of captured 15-μm-diameter microparticles, a reverse flow was applied from an outlet downstream of the filter 180 after removal of 5-μm-diameter microparticles at a waste outlet chamber. The cell focusing zone 108 included a channel that had flow focusing features 152 including a series of ridges having the slant geometry. The flow focusing features 152 in the embodiment tested are illustrated in FIGS. 4 and 4(a). FIGS. 4 and 4(a) show that the flow focusing features 152 include ridges 156 with a chevron configuration. The ridges 156 are oriented at an angle α of 70 degree to a longitudinal axis of the flow channel or to the apices of the ridges. The channel 144 in which the features 152 are disposed is 250 micrometer wide. The apex to apex spacing of adjacent ridges is 50 micrometer. The ridges 156 define a plurality of heights along the passage. In the illustrated embodiment, the height of some of the ridges 156 is a height "A" and the height of others of the ridges is a height "B". The height "A" is less than the height "B". For example, the height "A" can be 18 micrometers and the height "B" can be 40 micrometers. FIG. 4(a) illustrates that the cells of interest to be isolated in the device 100 pass under the ridges 156, that is the height "A" is greater than the size of the cells such that the cells do not become lodged in the ridges 156 blocking the flow.

The slant geometry directed the microparticles to the center of the channel 144 tightly without the assistance of sheath fluid. Finally, the focused microparticles were delivered to the single-cell trapping zone 112, and captured passively and sequentially in 18×18×16 μm$^3$ sized microwells 204. More generally, the wells may be sized such that they have a depth of between about 5 and 15% larger than the size of the constituent to be trapped in the wells.

Figures 2A, 2B, 2C:
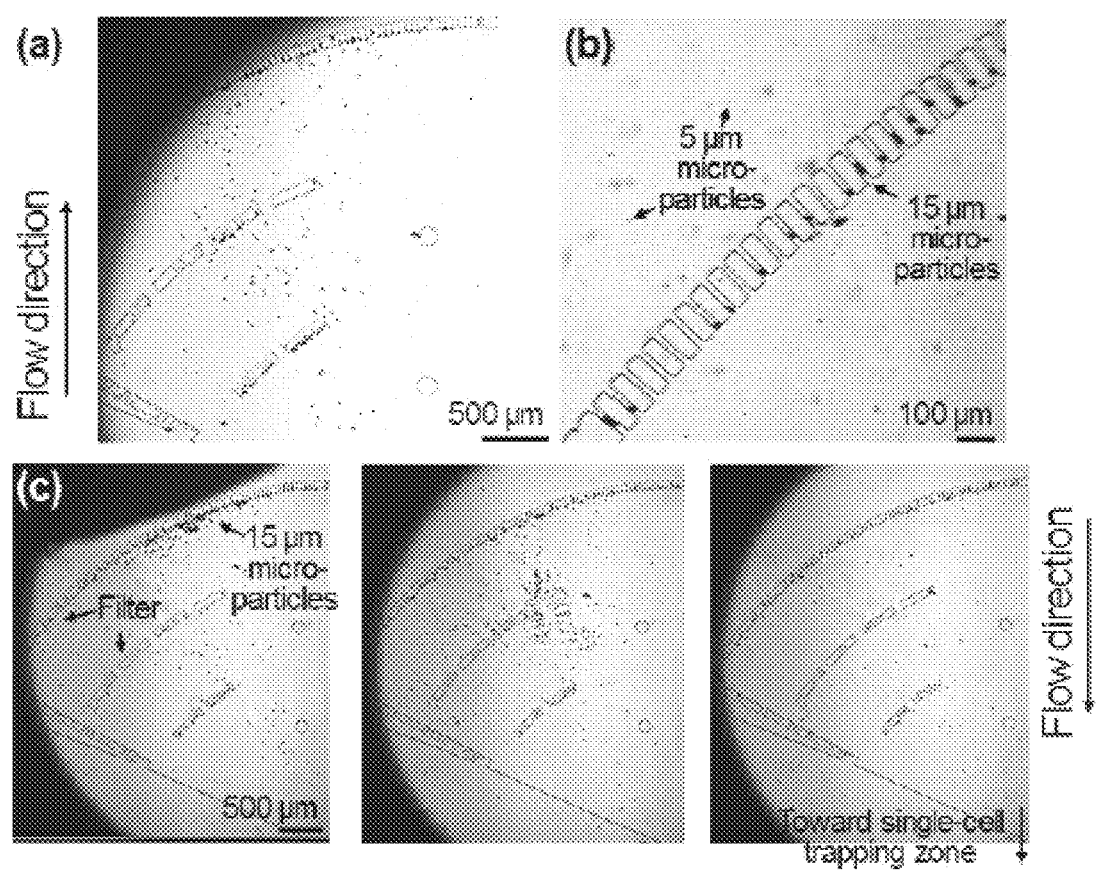
FIG. 2(a)-(b) shows the capture of particles of interest in a small particle filter.
FIG. 2(c) shows the flow of particles of interest away from a small particle filter.
Figures 2D, 2E, 2F:
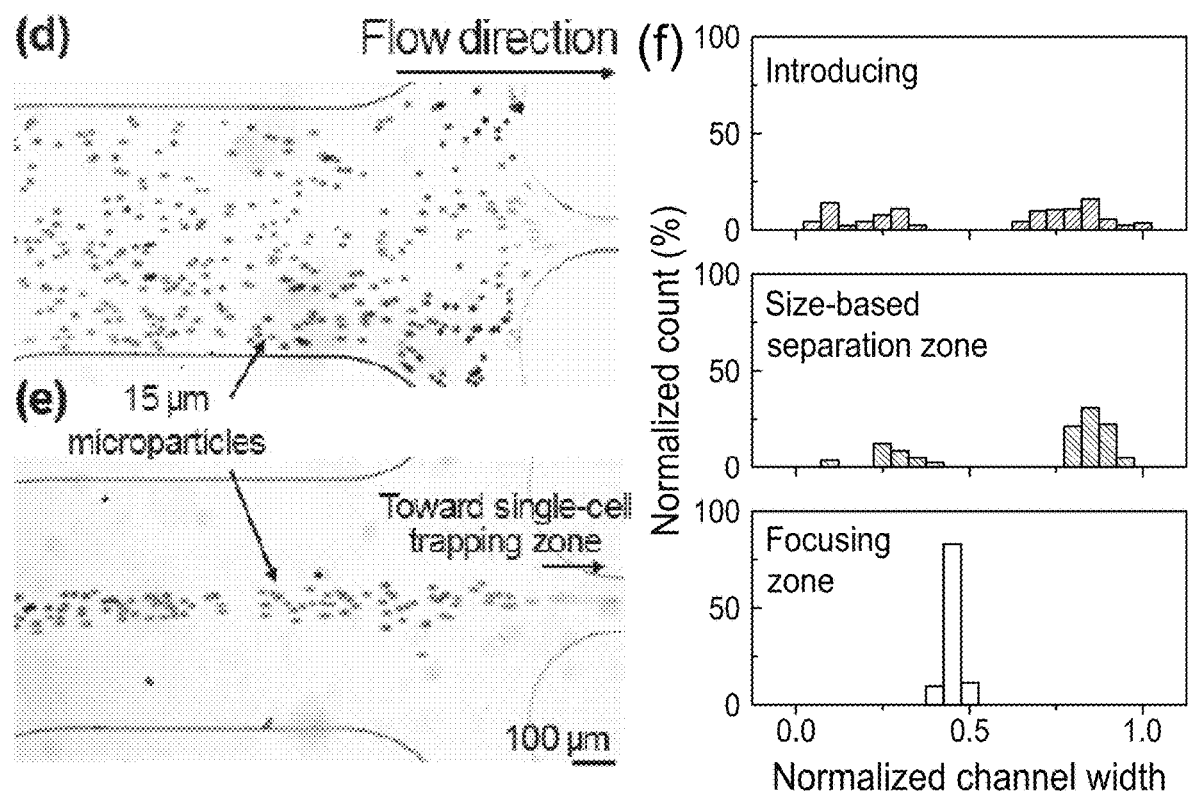
FIG. 2(d) shows wide dispersion of particles across a flow channel that does not have a cell concentrating zone.
FIG. 2(e) shows concentration of constituents in a central zone of a flow channel that has a cell concentration zone.
FIG. 2(f) shows distribution of constituents in the flow channel at various stages of a filtration and separation process.

In the size-based separation zone 112, the 15-μm-diameter microparticles were captured in the second filter 180 which was configured as a fan-shaped microfilter arrays with a 7 μm gap (FIG. 2a), while the 5-μm-diameter microparticles were rapidly washed out from the filter 180 (FIG. 2b). After removal of the 5-μm-diameter microparticles at the waste chamber, the flow direction is reversed, and then the 15-μm-diameter microparticles moved toward the single-cell trapping zone 112 (FIG. 2c). Whereas the microparticles remain unfocused in the non-grooved channel between the second filter 180 and the cell focusing zone 108, most of microparticles were successfully focused into the center of the microchannel of the focusing zone 108 along the slanted obstacle arrays of the focusing features 152, achieving a narrow focusing stream (FIG. 2e) compared to flow in a passage lacking the focusing zone 108 (FIG. 2d). The tightly focused 15-μm-diameter microparticles, which have the focusing positions of 240.82±13.86 μm, were transported to the single-cell trapping zone (FIG. 2f).

Figures 3A, 3B, 3C, 3D:
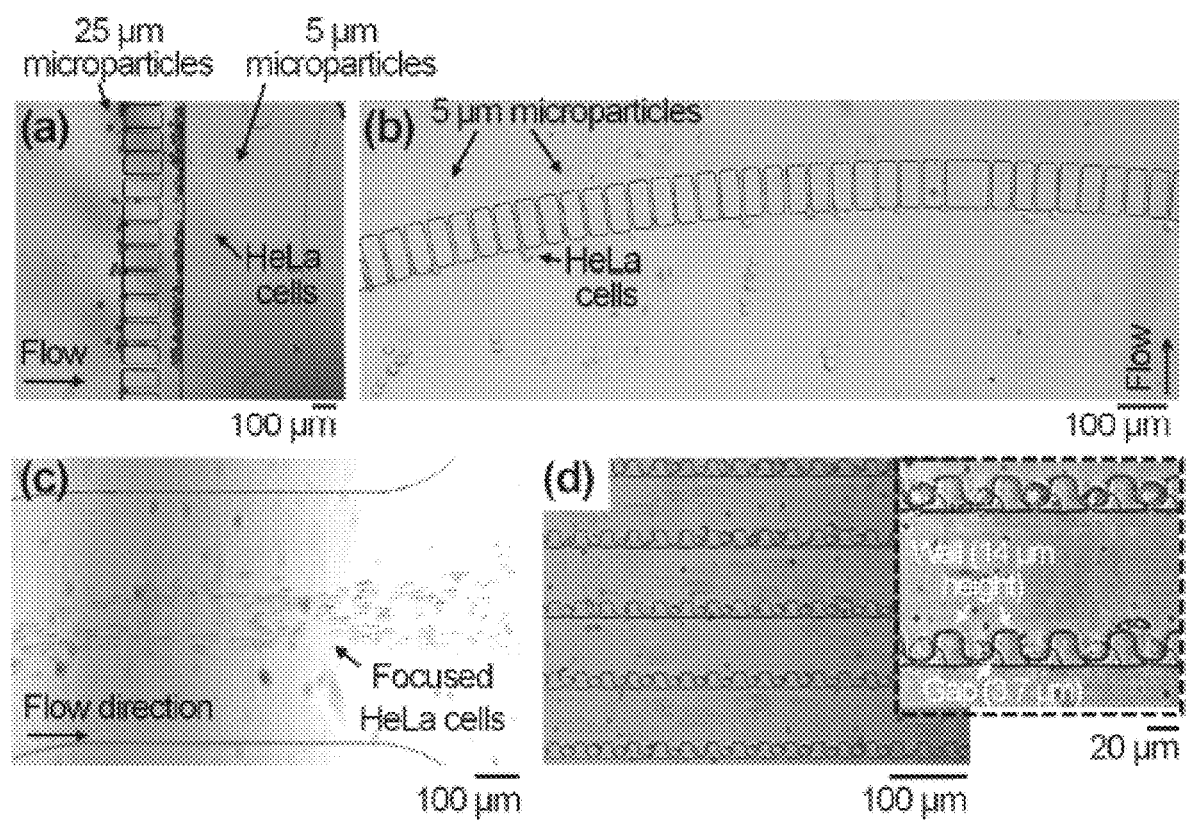
FIGS. 3(a)-3(d) illustrate an experiment in which HeLa particles were particles of interest and were separated from larger and smaller particles that were captured in appropriately sized micro-filters.

The ability of the platform to isolate mammalian cells from a mixture of HeLa cells, 5 and 25-μm-diameter microparticles was examined. In the prefiltering zone 104, the 25-μm-diameter microparticles were successfully captured in the filter 104, while HeLa cells and 5-μm-diameter microparticles were transported to the size-based separation zone (FIG. 3a). The transport of the cells was at a rate of 50 microliter/hour. HeLa cells were successfully captured and recovered from 5-μm-diameter microparticles by separating the 5-μm-diameter microparticles at the second filter 180 (FIG. 3*b*) and streaming the HeLa cells back toward the trapping zone 116 (FIG. 3*c*). FIG. 3*d* shows the microscopic images of 100 trapped HeLa cells in the array with a loading efficiency over 95%.

The approach described herein offers a number of benefits in sorting of complex microparticle samples. For example one of the advantages is that a continuous separation of microparticles requires only two inlets for sample delivery, which simplifies microparticle introduction without external force associated with electric, magnetic, acoustic or optical separators. As another example, the straightforward approach and the planar geometry of the microfluidic chip configured to sorting and/or trap cells enable easy integration with downstream dielectrophoresis (DEP) electrode for cell separation based on their viability and impedance analysis. Another advantage is that the cutoff diameters can be easily tuned by alteration of the size of the micropore filter.

Integrated Microfluidic Device for Single Cell Analysis

Figure 5B:
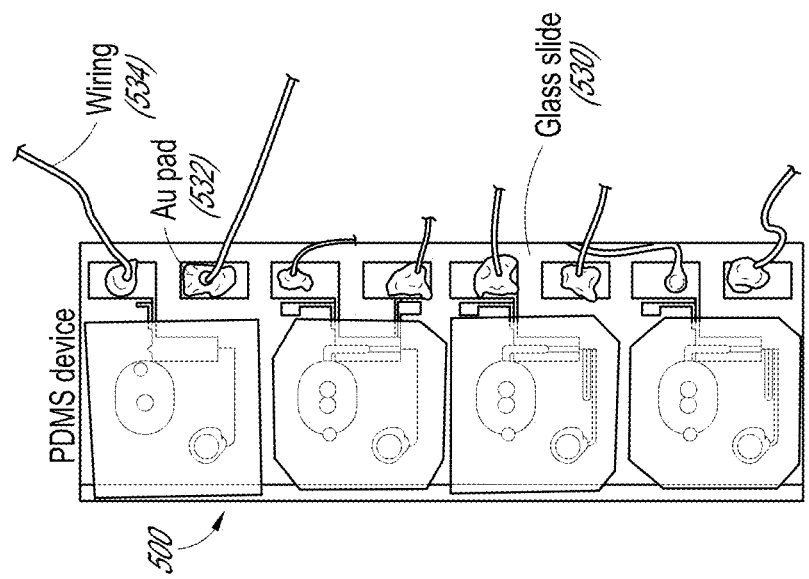
FIG. 5B is a photograph depicting an embodiment of an integrated microfluidic plant tissue single-cell analysis device.
Figure 5A:
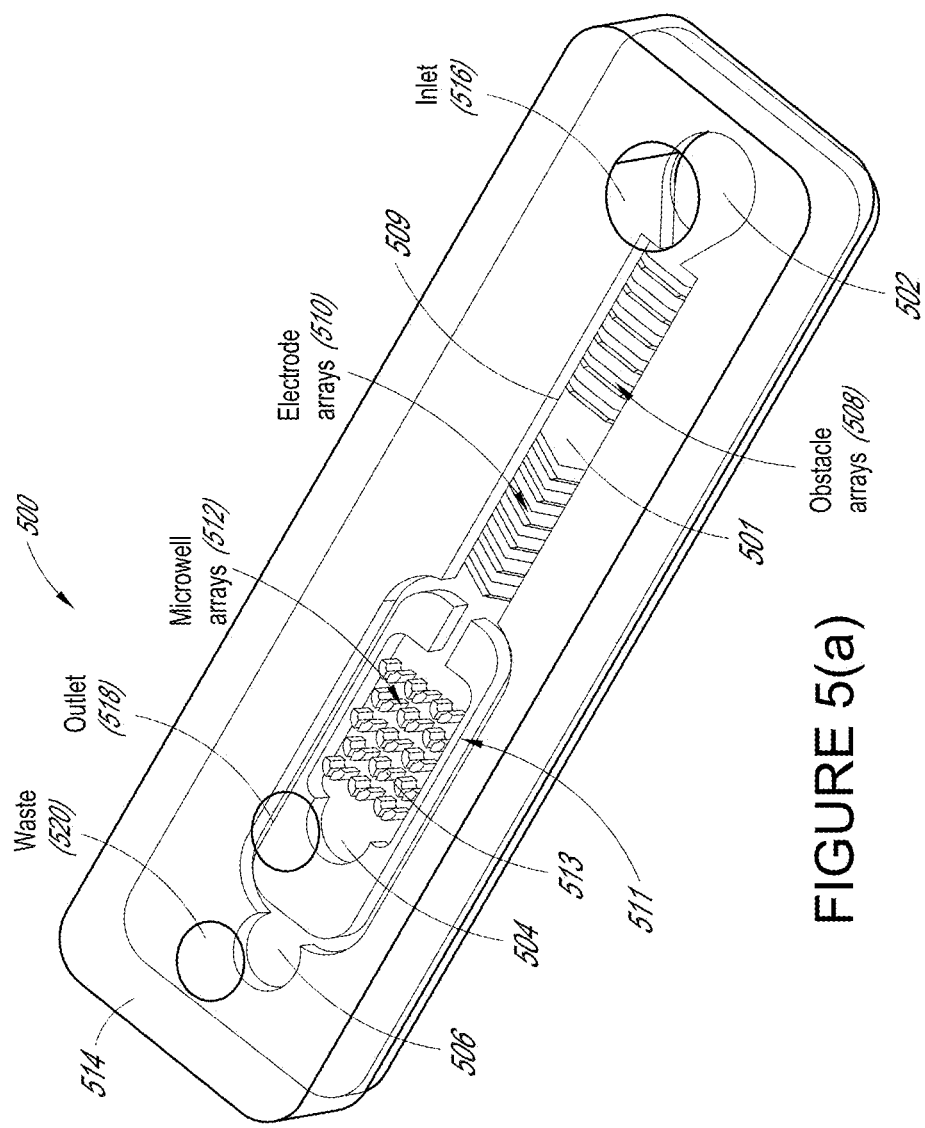
FIG. 5A is a schematic illustration of an embodiment of a microfluidic device including an encapsulated single-cell trapping array configured to trap an individual cell.

FIG. 5A schematically illustrates an embodiment of a microfluidic device 500 that integrates three different microfluidic platforms including cell focusing, dielectrophoretic (DEP) separation, and single-cell trapping. The integrated microfluidic device 500 illustrated in FIG. 5A can be used for assay of an individual plant cell. The integrated microfluidic device 500 comprises a microfluidic channel 501 having an inlet 502 through which a sample comprising a plurality of plant cells is introduced into the device 500 and an outlet 504 fluidically coupled to a waste chamber 506. The integrated microfluidic device 500 comprises an obstacle array 508 that is configured to focus the introduced sample of plant cells to a sidewall 509 of the microfluidic channel 501 by the hydrodynamic force. The integrated microfluidic device 500 further comprises an array of V-shaped electrodes 510 located downstream from the obstacle array 508. The electrode array 510 is configured to separate the introduced plant cells based on their viability. Once the plant cells are focused to the sidewall 509 of the microfluidic channel 501 by the obstacle arrays 508, only live cells are deflected by electric force and transported to a trapping region 511 located downstream from the electrode array 510 under the DEP regime. The trapping region is located includes a microwell array 512 configured as a single-cell trapping array to capture deflected live plant cells. Individual live plant cells that are deflected by the electrode array 510 to the center of the microfluidic channel 501 are trapped in the individual cell traps 513 of the microwell array 512 by hydrodynamic force. The integrated microfluidic device 500 comprises a thin layer of polymer material 514 (e.g., PDMS) disposed over the microfluidic channel 501 and the trapping region 511. The thin layer of polymer material 514 encapsulates the microwell array 512 to seal the plant cell sample from the environment. Holes 516, 518 and 520 can be punched in the layer of polymer material 514 corresponding to the inlet, the outlet and the waste chamber. The encapsulated integrated microfluidic device can be bonded to a substrate and configured for operation by providing electric and fluidic connections. For example, the encapsulated integrated microfluidic device 500 can be bonded to an Au-patterned glass slide 530 and the electric wires 534 are connected to a gold (Au) pad 532 patterned on the slide 530 to provide electric connections to the electrode array. FIG. 5B is a photograph of an encapsulated integrated microfluidic device bonded to an Au-patterned glass slide and provided with electrical connections.

Microfluidic devices configured for use in single-cell plant analysis as contemplated by this disclosure is not limited to the features shown in FIGS. 5A and 5B. Indeed this disclosure contemplates various other embodiments of microfluidic devices including a sample processing region (e.g., configured to perform sample filtering, sample focusing, sample sorting, etc.) and a single-cell trapping channel that can be used for single-cell plant analysis. In preferred embodiments, a microfluidic device is configured for isolation of individual plant cells, particularly microspores for the purpose of cell genotyping.

Microfluidic Chip Fabrication

Figure 7:
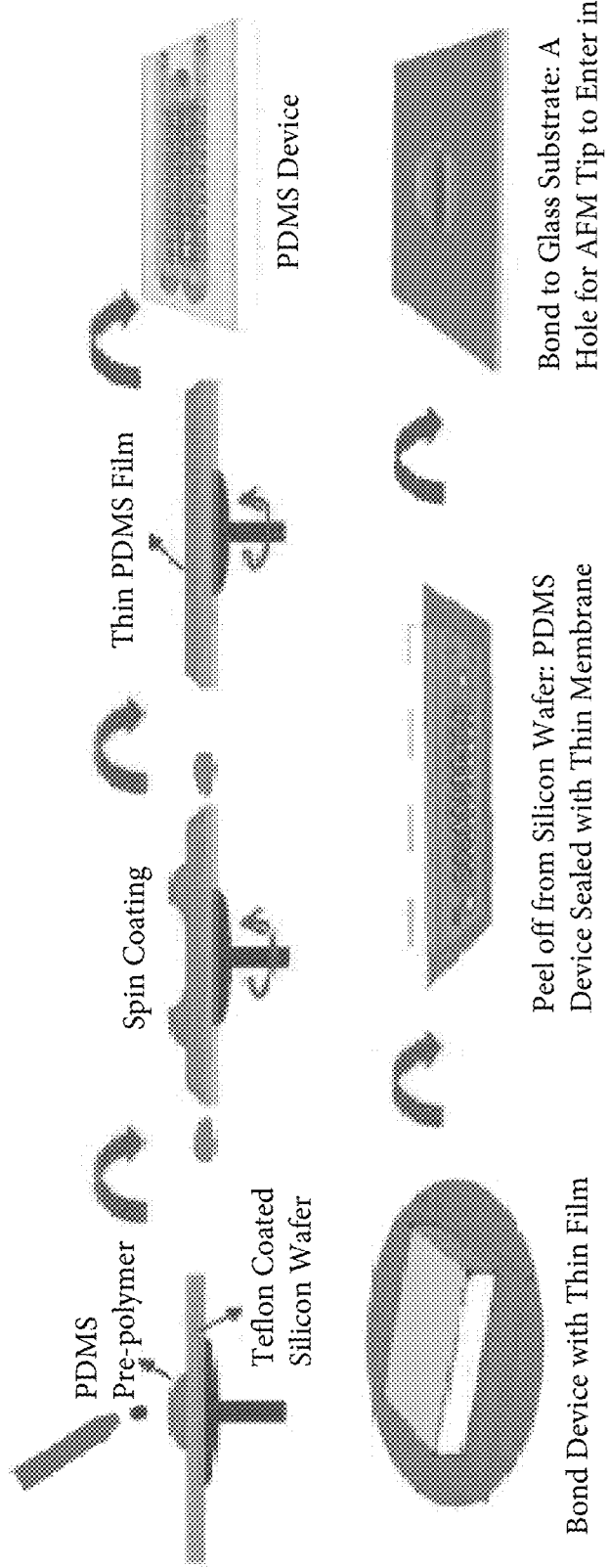
FIG. 7 schematic illustrates a fabrication process of microfluidic device including an encapsulated single-cell trapping array.

Microfluidic devices discussed herein can comprise a variety of materials such as polymers, plastics, glasses, and so on. For example, the microfluidic device discussed above with reference to FIGS. 5A and 5B can comprise PDMS. The microfluidic devices described herein can be fabricated using standard soft-lithography method with an SU8 master mold on a silicon substrate. An embodiment of a method of manufacturing the microfluidic devices described herein includes casting degassed PDMS pre-polymer mixture (mixed PDMS base with curing agent in a 10 to 1 ratio, Sylgard 184, Dow Corning Inc.) over a mold comprising microfluidic channels and other device features (e.g., obstacle array, electrode array, trapping array, etc.) and baking at a temperature of 65° C. overnight. The cured PDMS with embedded channels is subsequently diced by scalpel and removed from the master mold. Inlet and outlet holes can be punched through the PDMS slab by a 1.5 mm hole-puncher. The PDMS slab comprising the microfluidic device can be encapsulated by bonding to a thin PDMS membrane by oxygen plasma treatment. FIG. 7 illustrates an embodiment of a method of bonding the thin layer of polymer material to a fabricated microfluidic device and subsequently bonding the encapsulated microfluidic device to a substrate (e.g., a gold patterned glass substrate).

Spin Coating of the Thin Polymer Layer

Figure 6:
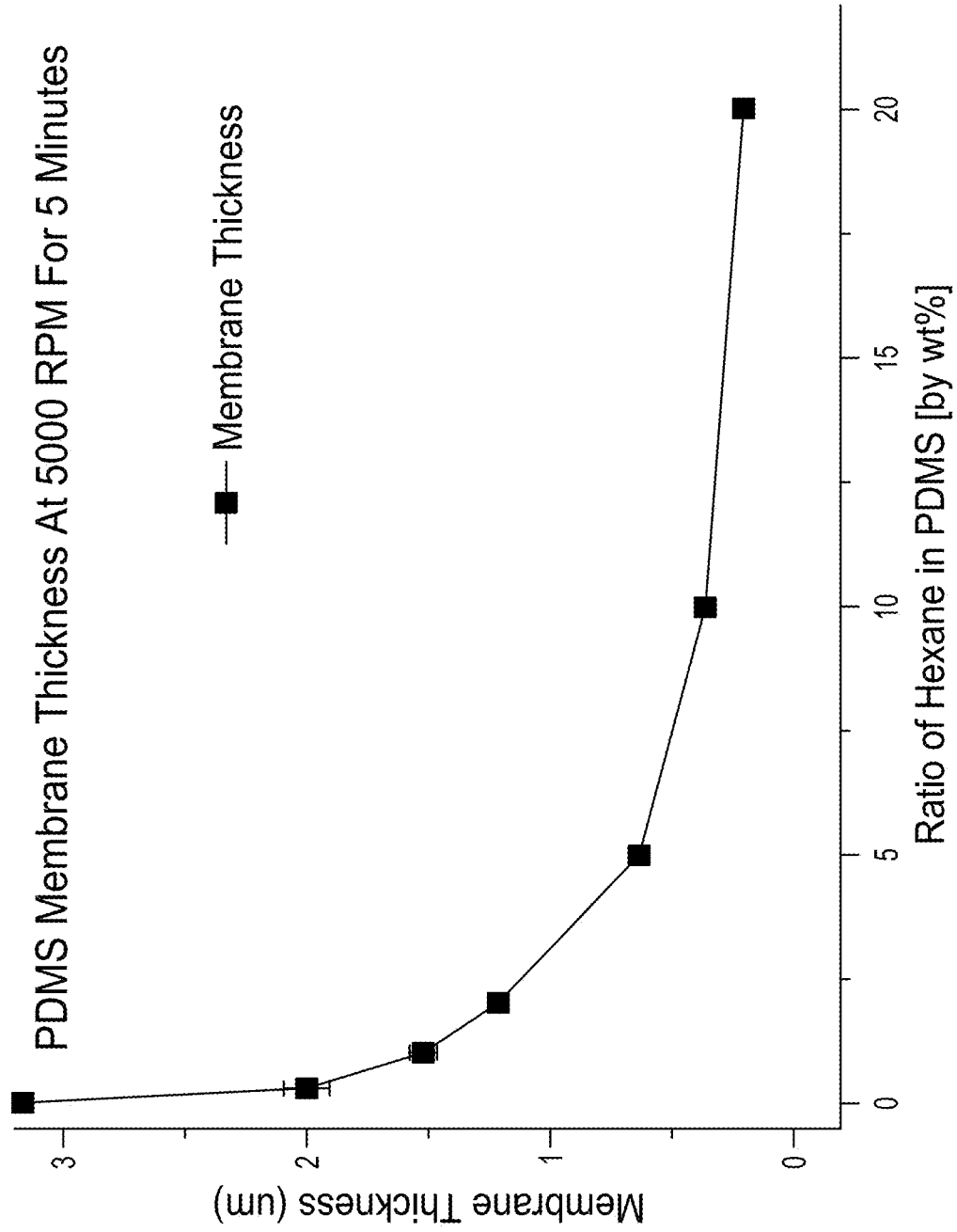
FIG. 6 illustrates a graph of PDMS membrane thickness and PDMS to Hexane dilution ratio.

The thin layer of polymer material that is used to encapsulate the trapping array can have a thickness less than 5 micron. For example, the thickness of the polymer material configured to encapsulate the trapping array can be between 0.5 microns and about 1 micron, between 1 micron and 2 micron, between 2 micron and 3 micron, between 3 micron and 4 micron, or between 4 micron and 5 micron. In an embodiment of a manufactured microfluidic device, an ultra-thin PDMS membrane with a thickness of 1 μm was fabricated by spin coating PDMS pre-polymer mixture's hexane (Sigma-Aldrich, St. Louis) diluent on a Teflon® coated silicon wafer at 5000 rpm for 5 min. Diluting PDMS pre-polymer mixture in hexane reduced its viscosity; therefore a much thinner membrane could be fabricated at similar spin coating parameters. The spin coated PDMS pre-polymer mixture's hexane diluent was baked at 120° C. for 45 min to evaporate the hexane, and at 65° C. overnight for curing. FIG. 6 shows the thickness of PDMS membranes with different PDMS to hexane ratios at same spin coating conditions, i.e. 5000 rpm for 5 min.

Chip Assembly

Bond-detach lithography can be used to seal the microfluidic device with the thin layer of polymer material. The sealed/encapsulated microfluidic device can be sunsequently bonded to a substrate (e.g., a gold patterned glass substrate) post oxygen plasma treatment. The gold patterned glass substrate can have a through-hole over the trapping array region to allow an external micro-manipulator (e.g., a dielectrophoretic nanotweezer (DENT), an atomic force microscope (AFM) probe, etc.) to pierce through the thin layer of polymer material and contact a cell trapped in the trapping array to perform an assay. Electric and fluidic connections can be provided to various parts of the microfluidic device. For example, the electrode array in various embodiments of the microfluidic device can be connected by wire bonds to gold pads on a gold patterned glass substrate. As another example, a plastic tube can be inserted through the inlet port to introduce sample (e.g., plant cell sample).

Individual Cell Trapping Array

Figure 8:
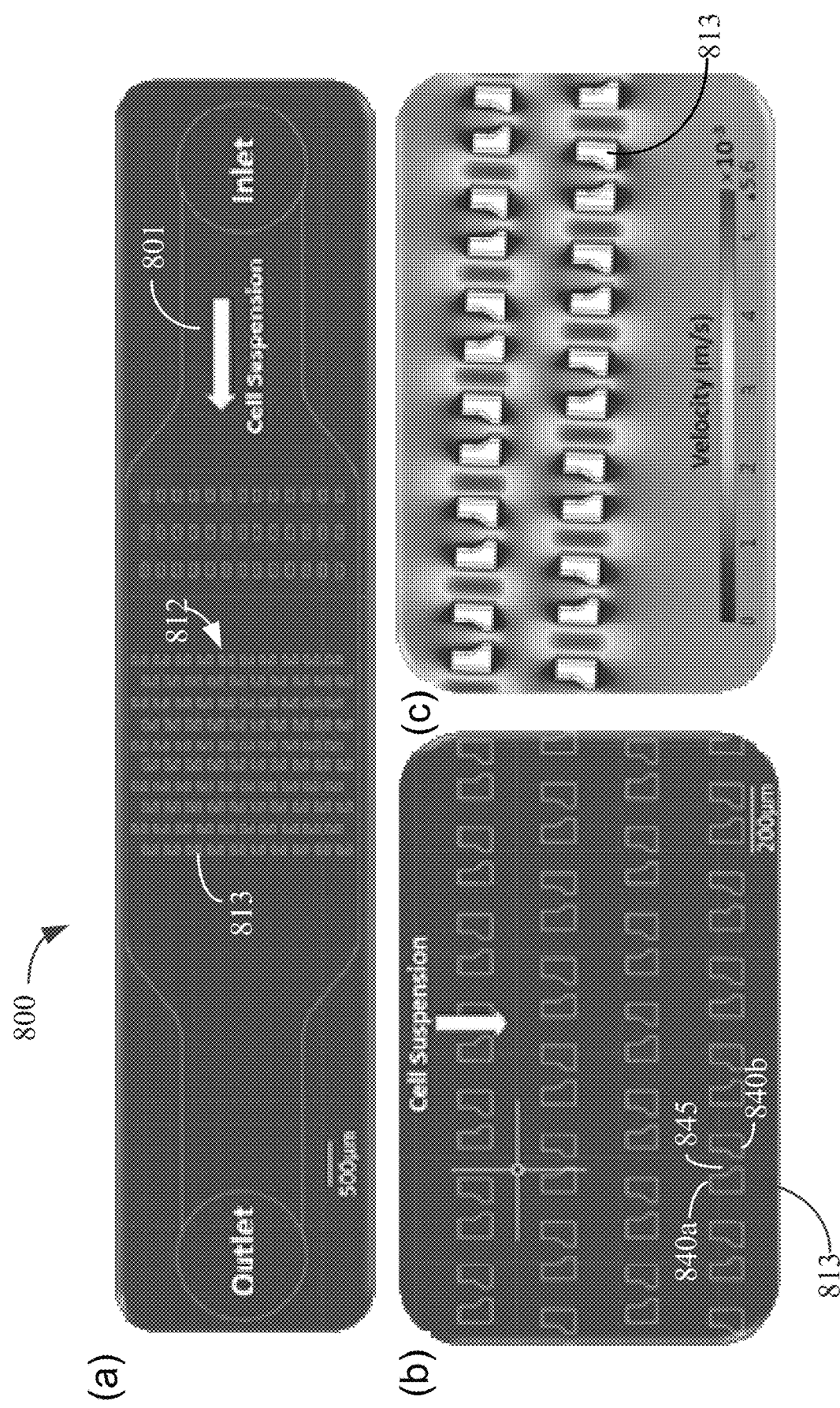
FIG. 8 illustrates design of a micro-well array. Panel (a) is an AutoCAD design of a microwell array configured to trap an individual plant cell. Panel (b) is a magnified image of the microwell array depicted in Panel (a). Panel (c) is a Comsol simulation of the velocity profile through the microwell array at flow rate of 10 µL/min.

FIG. 8 is a schematic illustration of a microfluidic device design 800 comprising a microfluidic channel 801 coupled to a trapping array 812. The design of the trapping array 812 comprising a plurality of individual cell traps 813 that are configured to trap individual cells from the sample is shown in FIG. 8. The trapping array 812 can be similar to the trapping array 512 discussed above. Each individual cell trap 813 can be configured as a microwell. For example, each individual cell trap 813 can be similar to the microwell 513 discussed above. In various embodiments, each individual trap 813 can include a groove or a concave shaped (e.g., cup-shaped) region 845 between two support structures 840a and 840b as illustrated in Panel (b) of FIG. 8. In various embodiments, each individual cell trap can be configured as a U-shaped region, a C-shaped region, a H-shaped region, a S-shaped region or some other shape that facilitates trapping individual cells. The groove or a concave shaped region 845 can be configured to have a size approximately equal (e.g., within ±10%) to the size of the individual cell it is configured to trap. For example, when the microfluidic device is configured for single cell analysis of plant cells, each individual trap can have a groove that has a dimension (e.g., width) that is approximately 75 µm, which is similar to the average diameter of plant cells. In the case of microspores, size can vary greatly between species and developmental stage. The trapping array accommodates for the size variability. The trapping array 812 can include a plurality of rows of microwells or individual cell traps 813 as depicted in Panels (a) and (b) of FIG. 8. In various embodiments, the microwells of each row can be aligned with the gaps between microwells of the previous row. The microfluidic channel 801 and the microwells are configured such that the flow velocity in the gap (e.g., between individual microwells) is higher than the flow velocity in the microwell as depicted in Panel (c) of FIG. 8. This ensures that cells that escape from the gaps are pushed into microwells in the next row.

Figure 9A:
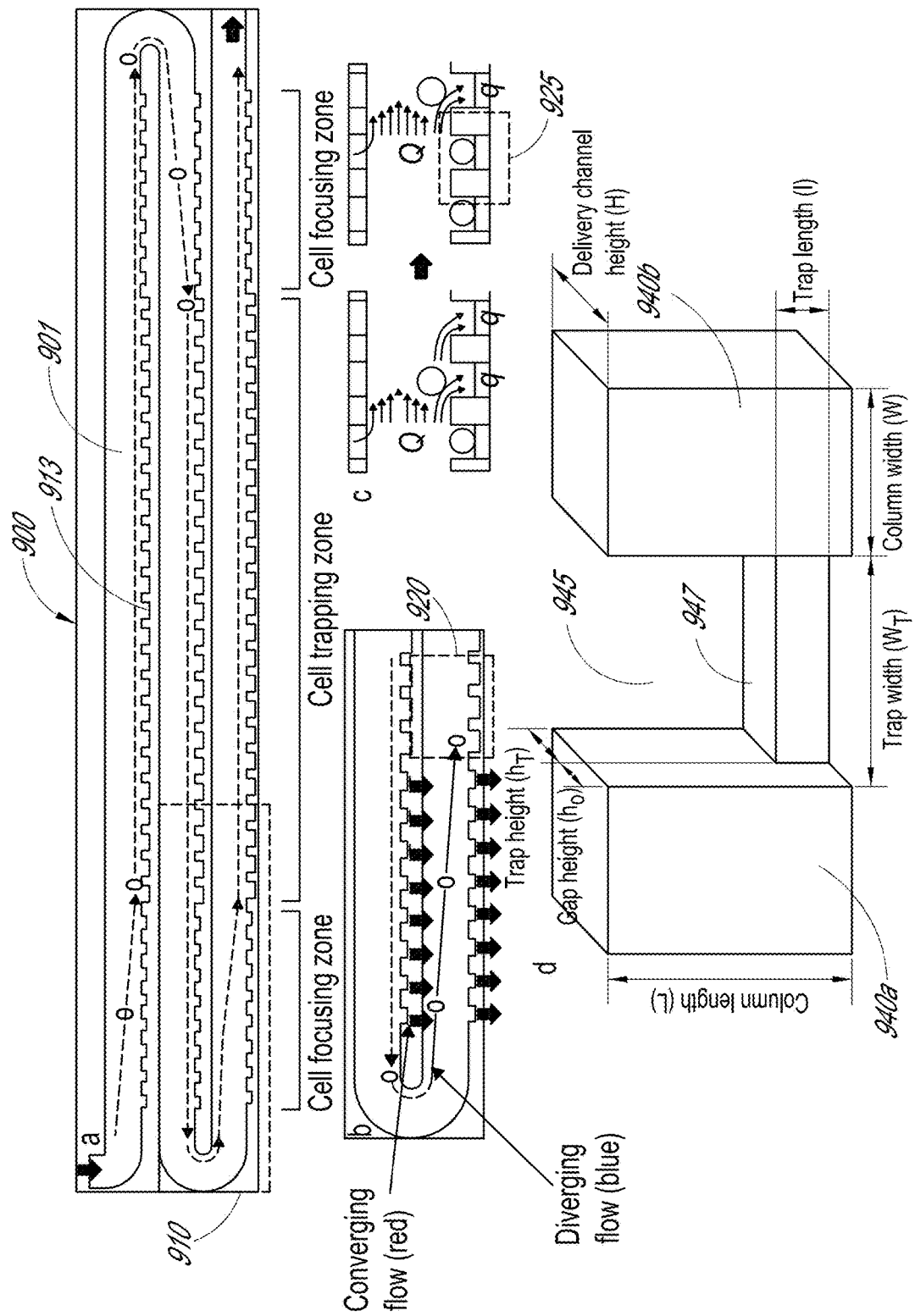
FIG. 9A illustrates a single-cell trapping array.
Figure 9B:
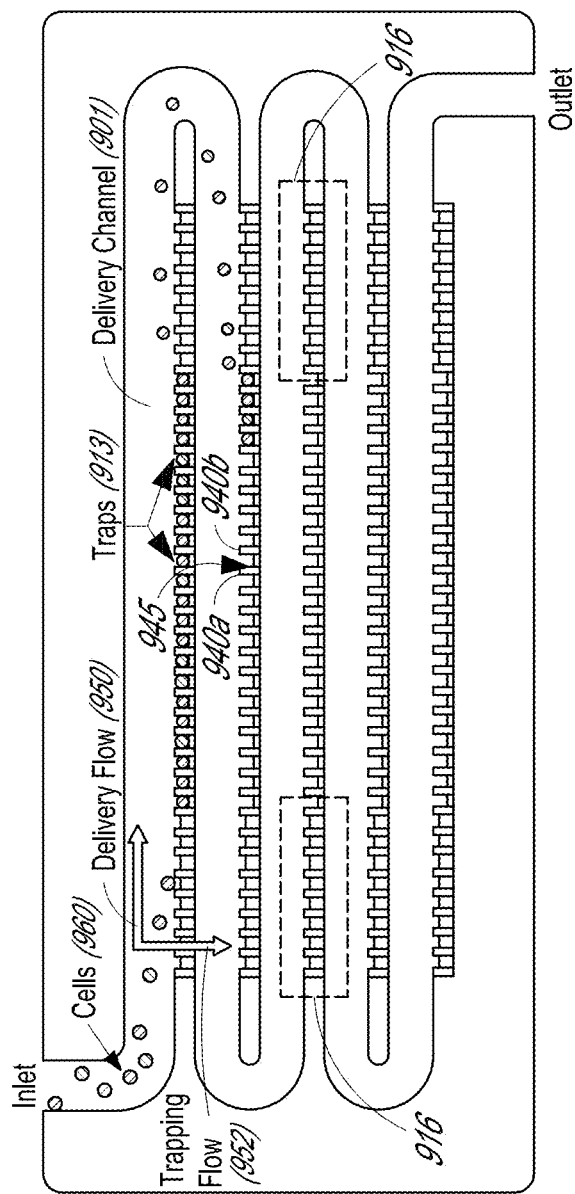
FIG. 9B schematically illustrates a serpentine microfluidic channel comprising an array of single-cell traps.
Figure 9D:
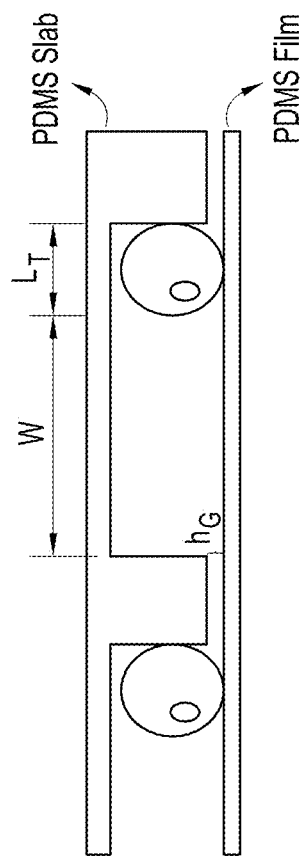
FIGS. 9C and 9D schematically illustrate a single-cell trap of the trapping array.
Figure 9C:
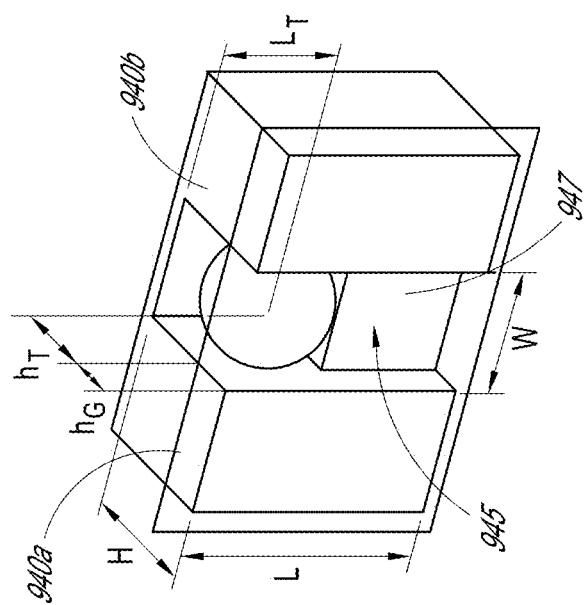

FIG. 9A illustrates another embodiment of a trapping array based on a design schematically illustrated in FIG. 9B. The trapping array 900 shown in FIGS. 9A and 9B comprises a serpentine cell delivery microfluidic channel 901 with an array of trapping units 913 disposed along an edge of the channel 901. The serpentine delivery channel includes a plurality of turning zones such that the trapping units of the trapping array 900 are arranged in a plurality of rows. The trapping array 900 includes a plurality of dummy traps 916 disposed at the turning zones of the channel 901. The dummy traps 916 are configured to focus cells towards the trapping units 913. Each trapping unit 913 includes a groove (e.g., a rectangular groove) 945 disposed between two support structures 940a and 940b. The geometry of each trapping unit 913 is schematically illustrated in FIG. 9C, FIG. 9D and Panel (d) of FIG. 9A. In various embodiments of the trapping unit 913, the groove 945 can include a ledge 947 to receive and trap an individual cell as depicted in FIG. 9C and Panel (d) of FIG. 9A. As noted from Panel (d) of FIG. 9A, for various embodiments of the trapping unit 913, the height of the trap ($h_T$) is smaller than the height of the delivery channel (H), generating a gap area ($h_G=H-h_T$). FIG. 9A comprises four panels (a), (b), (c) and (d). Panel (a) of FIG. 9A is a schematic drawing of the three rows of the array with the trajectory of cells. Panel (b) corresponds to the boxed region 910 in Panel (a) showing cell focusing mechanism. Panel (c) corresponds to the boxed region 920 in Panel (b) and Panel (d) corresponds to the boxed region 925 in Panel (c). As depicted in panel (b) when the cells flowing through the serpentine delivery channel 901 are turned by the turning zones, they experience a converging flow as depicted by red arrows in panel (b) and a diverging flow as depicted by the dashed line in panel (b). The flow pattern along the dummy traps of the turning zone 916 focus cells towards the trapping units 913. As depicted in panel (c) the cells flowing through the channel 901 in the vicinity of the trapping units 913 experience two flow streams: a delivery flow (Q) and a perpendicular flow (q). The delivery flow (Q) is depicted as delivery flow 950 in FIG. 9B amd the perpendicular flow (q) is depicted as perpendicular flow 952 in FIG. 9B.

Referring to FIG. 9B and panel b of FIG. 9A, the perpendicular stream 952 is directed along the width of serpentine channel 901 and can cause the cells to cross each row of the delivery channel 901 and be pushed to into various trapping units 913 as depicted in Panel (c) of FIG. 9A and FIG. 9B. The dummy traps 916 at the turning zone of each row can help generate perpendicular flow to focus cells towards the traps as depicted in Panel (b) of FIG. 9A. Accordingly, in the embodiment illustrated in FIGS. 9A and 9B, cells are delivered to the individual trapping units 913 sequentially by the horizontal delivery flow 950, and pushed into the traps by the perpendicular pushing flow 952. Since the trap size is similar to the cell size, when a cell occupies a trap, it physically excludes the next cell and reduces the possibility of trapping multiple cells. In an embodiment of a microfluidic device, in order to trap 100 single cells sequentially, the delivery channel can be configured as a 5-row format, with 20 traps in the middle of each row, and dummy focusing traps in the beginning and end of each row.

Figure 10:
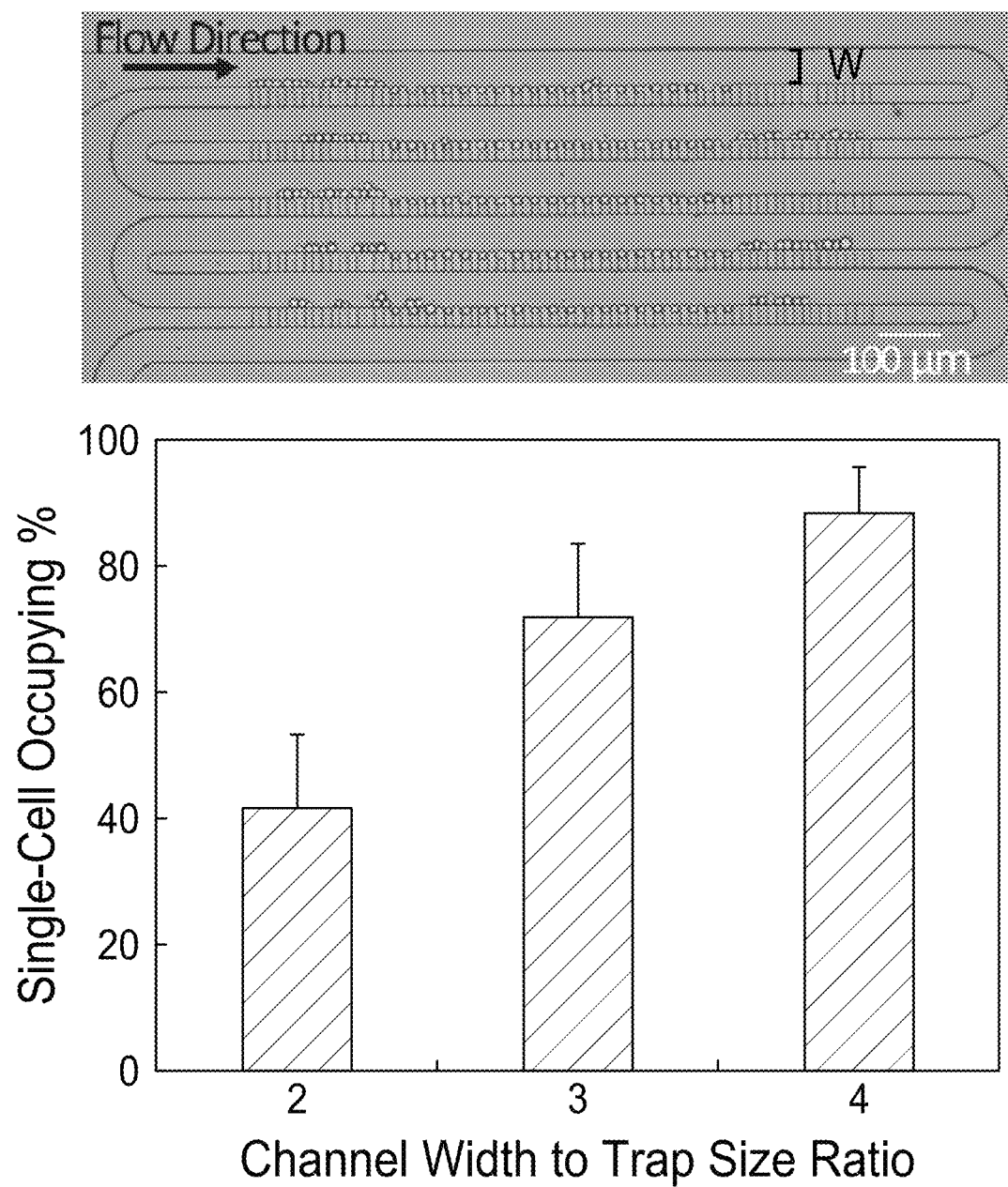
FIG. 10 illustrates the dependence of the percentage of single-cell occupancy in a trapping array to the ratio of channel width (W) to trap size ($W_T$).

It was found that the trapping efficiency which is related to the percentage of single cell occupancy does not depend on flow rate, but instead depends on the resistance ratio between horizontal delivery flow and perpendicular trapping flow, which in turn depends on the geometry of the trapping array. For example, the ratio of main channel width to trap size can be modified to vary the trapping efficiency. With every other parameter kept consistent, the main channel width, W can influence resistance ratio between horizontal delivery flow and perpendicular trapping flow. For example, when a width (W) of the main channel is less than a threshold width ($W_{thr}$), the delivery flow may be too strong resulting in empty traps. When a width (W) of the main channel is greater than a threshold width ($W_{thr}$), the delivery flow may not be strong enough compared to the perpendicular flow resulting in multiple cells clogging at one trapping unit. The threshold width ($W_{thr}$) can be about four times the diameter of the cells to be trapped. In some embodiments, a 4:1 ratio between the main channel width (W) and trap size may be sufficient to achieve high trapping efficiency (e.g., greater than 80%) as depicted in FIG. 10.

Accordingly, the trapping efficiency can be modified by modifying the design parameters of the trapping array. Thus, embodiments of a microfluidic device comprising a trapping array designed in accordance with the principles discussed above can be adaptable to a wide range of the input flow rates, and can be easily integrated with other microfluidic components. As all the parameters of this single-cell trapping array can be scaled up and down relative to the target cell diameter, therefore, this single-cell trapping design is adaptable for isolation cells with arbitrary diameters individually.

Dielectrophoresis Based Cell Sorting

Figure 11:
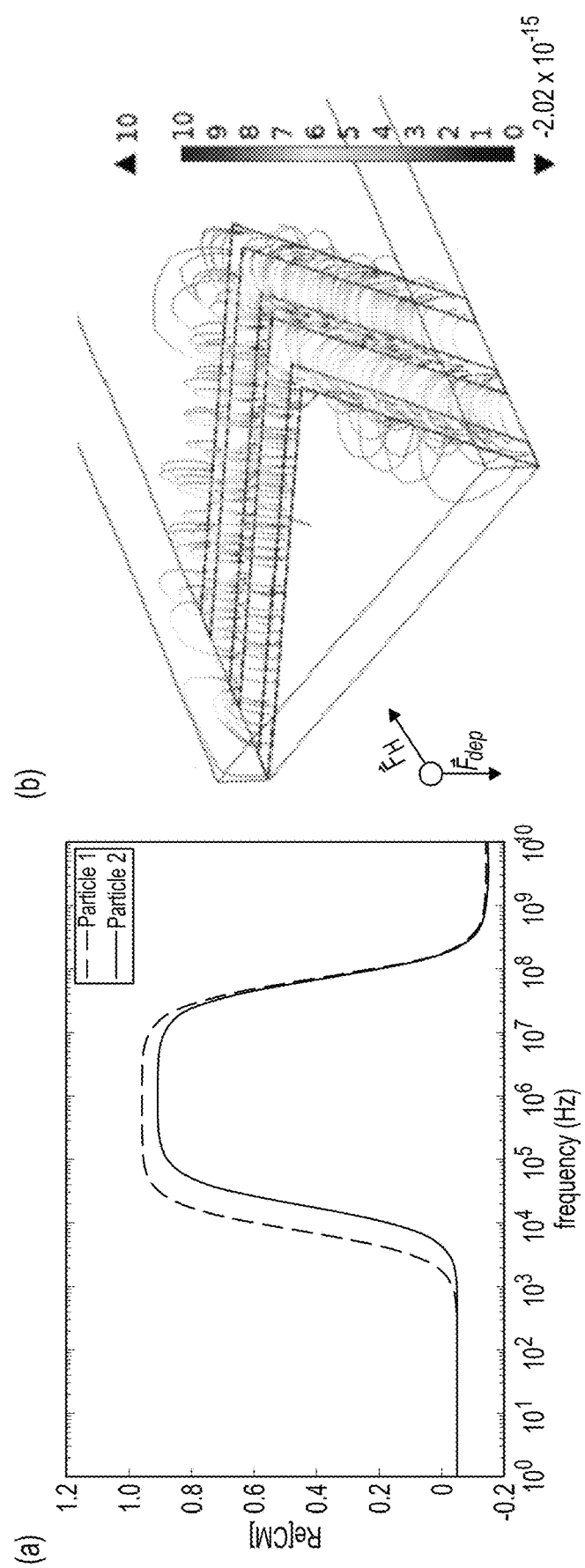
FIG. 11 illustrates the use of a V-shaped electrode array to sort live cells and dead cells sort via dielectrophoresis (DEP). Panel (a) is a Clausius-Mossotti factor plot for 2 single shell uniform spherical particles with different dielectric properties. Panel (b) is a force diagram of a healthy cell when subject to a non-uniform electric field between the V-shaped electrodes array.

Dielectrophoresis (DEP) is a phenomenon in which a force is exerted on a dielectric particle when it is subjected to a non-uniform electric field. When the Clausius-Mossotti (CM) factor is negative (e.g., for frequencies below $10^3$ Hz), the particle will move away from high field region, if the CM factor is positive (e.g., for the frequencies from $10^3$ to $10^8$ Hz), the particle will move toward the direction of increasing electric field as depicted in Panel (a) of FIG. 11. Furthermore, the direction of DEP mobility at a particular frequency can be sensitive to the cell size/shape and the protein density on the cell membrane and cell wall, which vary widely for different species, and is distinct for live/dead and diseased/healthy cells. As a result, this phenomenon is being used in many research applications as a label-free method to sort and manipulate microparticles, nanoparticles and biological cells. The COMSOL electrostatic simulation depicted in Panel (b) of FIG. 11 simulates the electric field converging on the surface of the electrodes when an electric potential is applied between them; hence, at frequencies where the CM factor is positive, the cells will be pulled toward the electrode surface. Additionally, there is a hydrodynamic force induced by fluid flow pushing the cell along the microchannel. The combined forces acting on the cell can move it along the electrode surface.

Figures 12A, 12B, 12C, 12D:
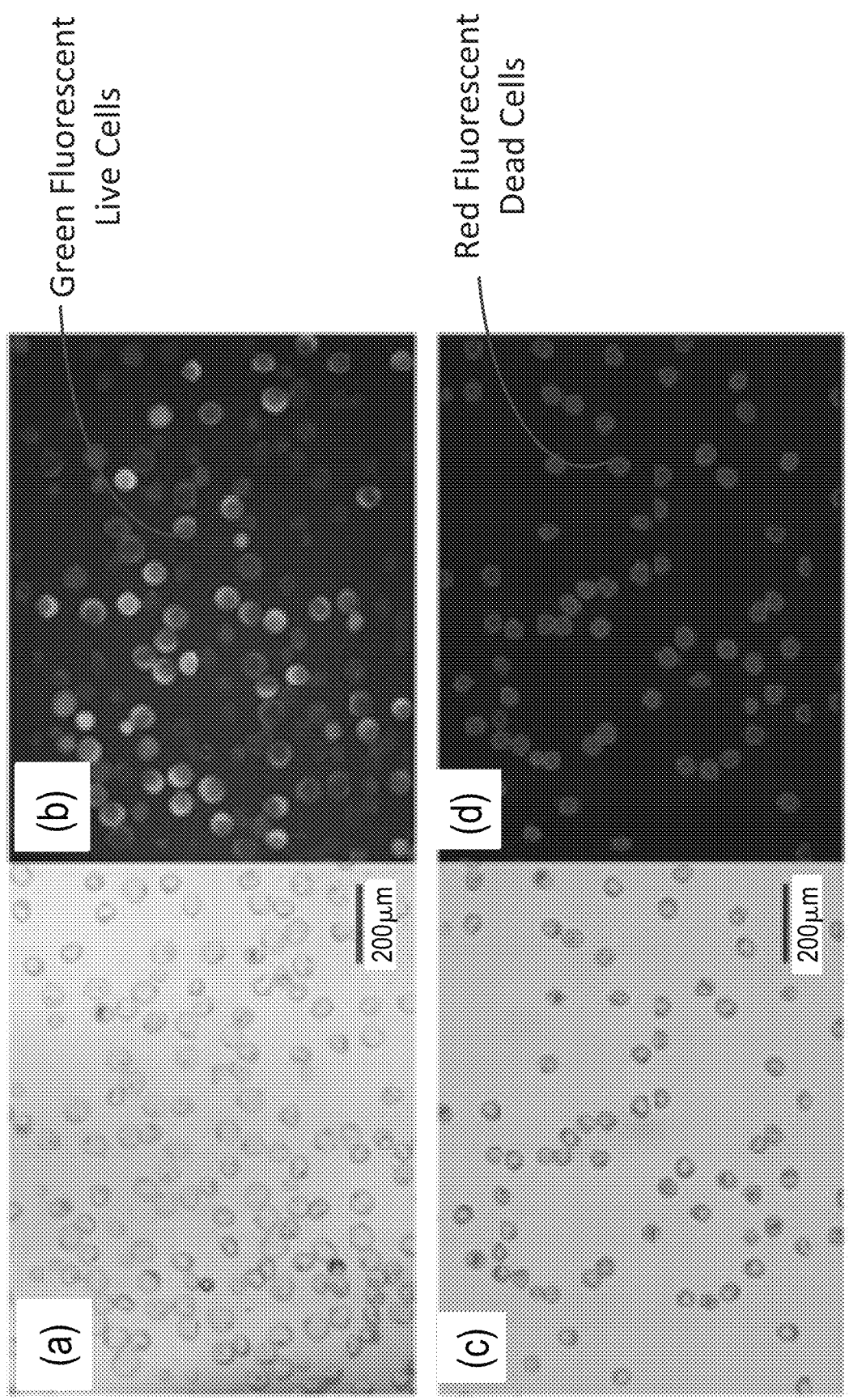
FIG. 12 illustrates result of live/dead plant cell sorting by DEP using the V-shaped electrode array. Panel (a) is a bright-field microscope image of live plant cells and Panel (b) is a fluorescence image live plant cells. Panel (c) is a bright-field microscope image of dead plant cells stained with Calcein AM and ethidium homodimer-1 and Panel (d) is a fluorescence image of dead plant cells of stained with Calcein AM and ethidium homodimer-1. Panel (e) is a stacked microscopic image from a video recording capturing the experimental results of continuous live and dead separation of the SX19 cells. Bright-field and fluorescence images of separated SX19 cells (Panel (f) and Panel (g)) with DEP deflection and (Panel (h) and Panel (i)) without DEP deflection.
Figures 12E, 12F, 12G, 12H, 12I:
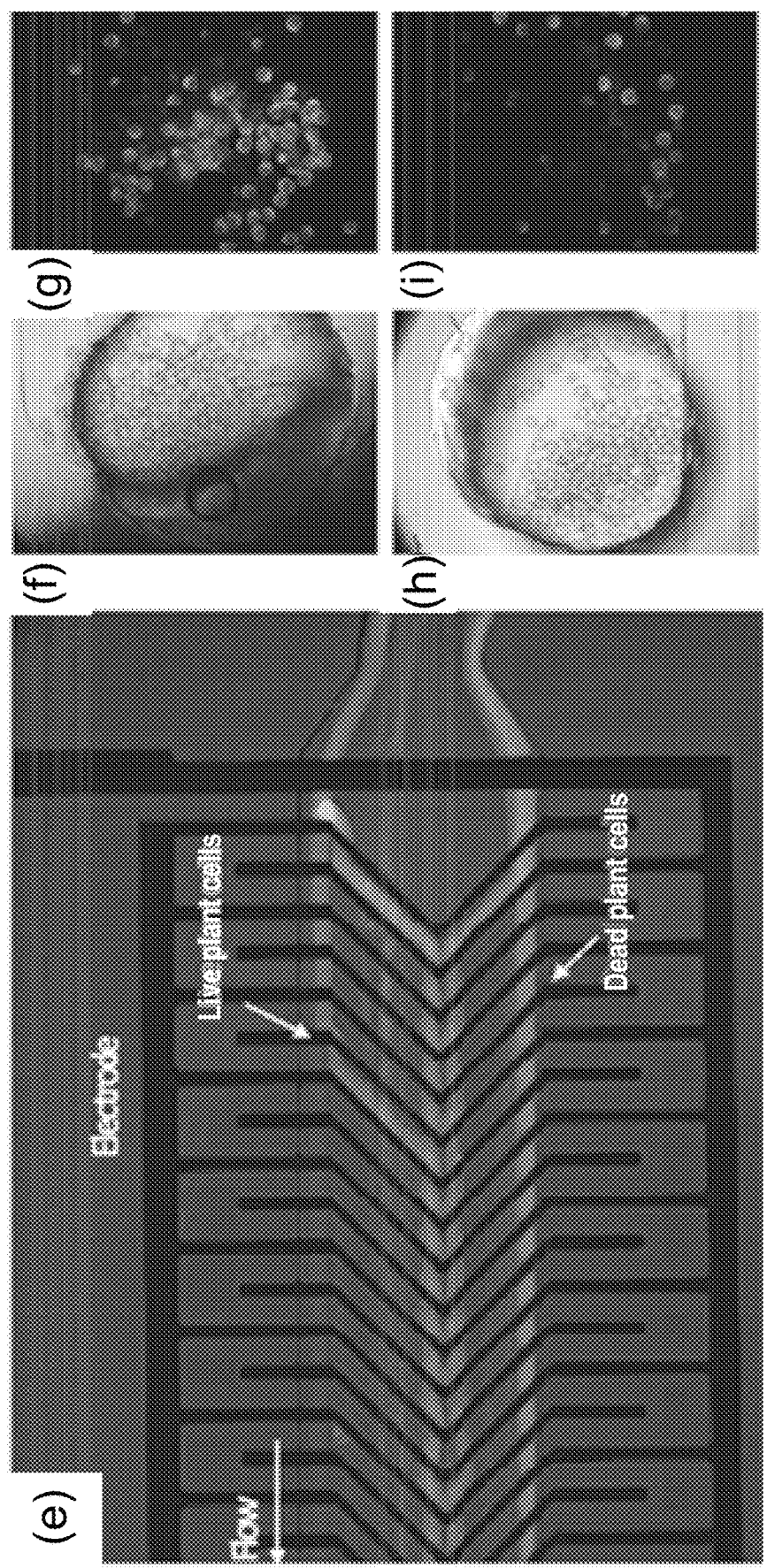
Figure 13:
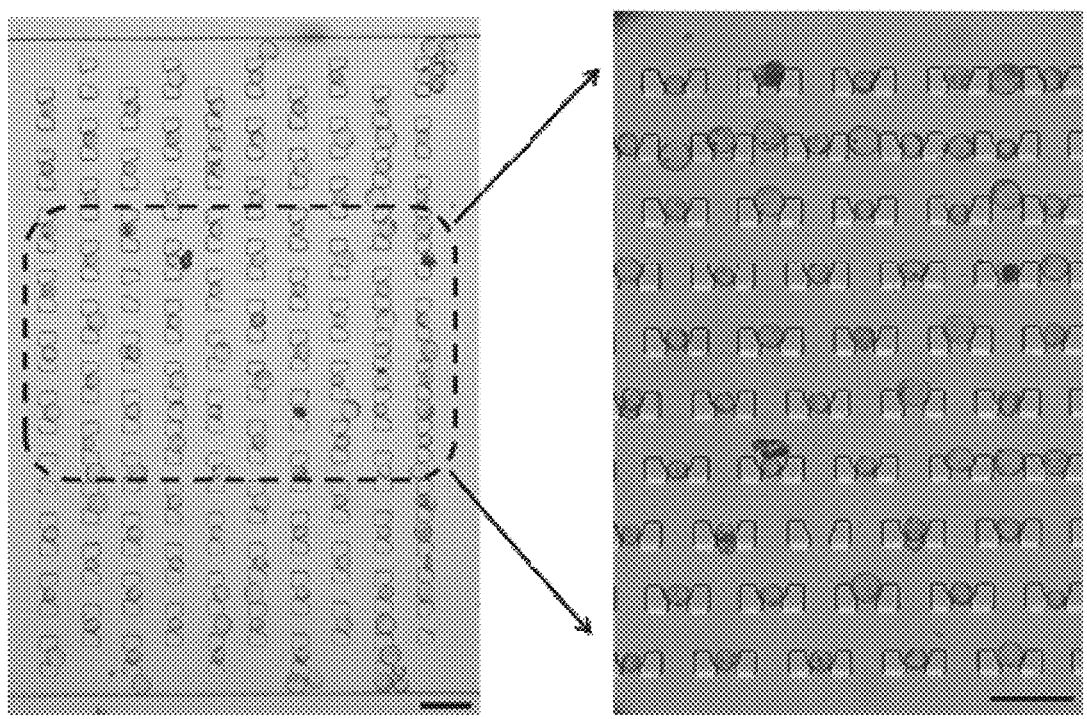
FIG. 13 illustrates individual plant cells trapped in a single-cell array.

Referring to the microfluidic device depicted in FIGS. 5A and 5B, when introduced plant cell sample is focused by the obstacle array enters the V-shaped electrode region, a positive DEP force pushes live plant cells from the focused plant cell sample toward the center of the microchannel. For example, the green fluorescent live cells depicted in Panels (a) and (b) of FIG. 12 experienced a higher positive DEP force that induced a lateral displacement which manipulated them into the microchannel center as shown in Panel (e) of FIG. 12. On the other hand, the red fluorescent dead cells depicted in Panels (c) and (d) of FIG. 12 could only be moved along the flow direction without any lateral displacement. To evaluate the effect of electric field on cell viability, the plant cells were stained after DEP separation. As a result, the sorted sample showed that the live cells were greatly recovered at the center outlet chamber S1 (as depicted in Panels (f) and (g) of FIG. 12), and the number of green cells was reduced in the side outlet chamber S2 (Panels (h) and (i) of FIG. 12). After live/dead cell sorting, viable plant cells deflected towards the center of the microfluidic channel flow into the microwell array and can be trapped individually. A single-cell trapping array configured to trap individual plant cells is shown in FIG. 13. The single-cell trapping array can be based on the design depicted in FIG. 8 discussed above. For example, a width of an individual cell trap can be about 75 µm. Plant cells were introduced into the chip at a flow rate of 10 µL/min, with a concentration of $10^4$ cells/mL. The parameters of the single-cell trapping array were optimized to fill 100 traps in less than 1 minute. The trapping efficiency can be greater than 80%.

Single-Cell Analysis without Lysing

Various embodiments of microfluidic devices discussed herein that are configured to trap individual cells in an individual trapping array, can be used to perform single-cell analysis. Single-cell analysis can have several advantages over conventional bio-molecular analysis techniques. Conventional bio-molecular analysis techniques are usually bulk assays, in which the average response from a population of cells is measured and analyzed. However, conventional bio-molecular analysis techniques have several disadvantages. For example, for various cell populations, the average cannot represent every specific cell. Therefore the unique characteristics of single cells may be obscured. Moreover, bulk assay needs a large amount of staring material, but in many clinical researches, only a small amount of material is available. Therefore in recent years, single-cell analysis has become attractive. Single-cell analysis can reveal the heterogeneity and stochastic effect among cell populations, which can be advantageous in determining cell fate and key cellular activities. It can also help in interrogating fundamental cellular mechanisms, and provide data from minority sub-populations that may otherwise be obscured in bulk assays. Furthermore, as the analysis scales are reduced to single-cellular level, only a small amount of stating material is sufficient to perform single-cell analysis making it suitable for rare cell studies.

Microfluidic devices including microfluidic devices described herein have several advantages that make them useful for single-cell analysis. For example, microfluidic devices have reduced sample volume, improved analysis efficiency, ease of scaling up and multi-step integration. Various existing microfluidic devices can be sealed devices in which reactions are blocked within the chip. Furthermore, it may not be practical for external equipment to access samples inside the sealed microfluidic devices. Additionally, it may not be possible to extract inner-cellular compounds while performing single cell analysis without cell lysing in various existing microfluidic devices.

Embodiments of microfluidic devices discussed herein, such as, for example, the devices depicted in FIGS. 5A and 5B can solve some of the deficiencies with existing microfluidic devices. For example, the thin layer of polymer material that encapsulates the individual traps that are configured to trap cells for single-cell analysis is configured to seal the trapped cells from the environment while also allowing an external instrument (such as a DENT or an AFM probe) to pierce through the polymer layer and extract cellular compounds from the trapped cells without cell lysing. This is discussed in greater detail below with reference to FIGS. 14A and 14B.

Figure 14A:
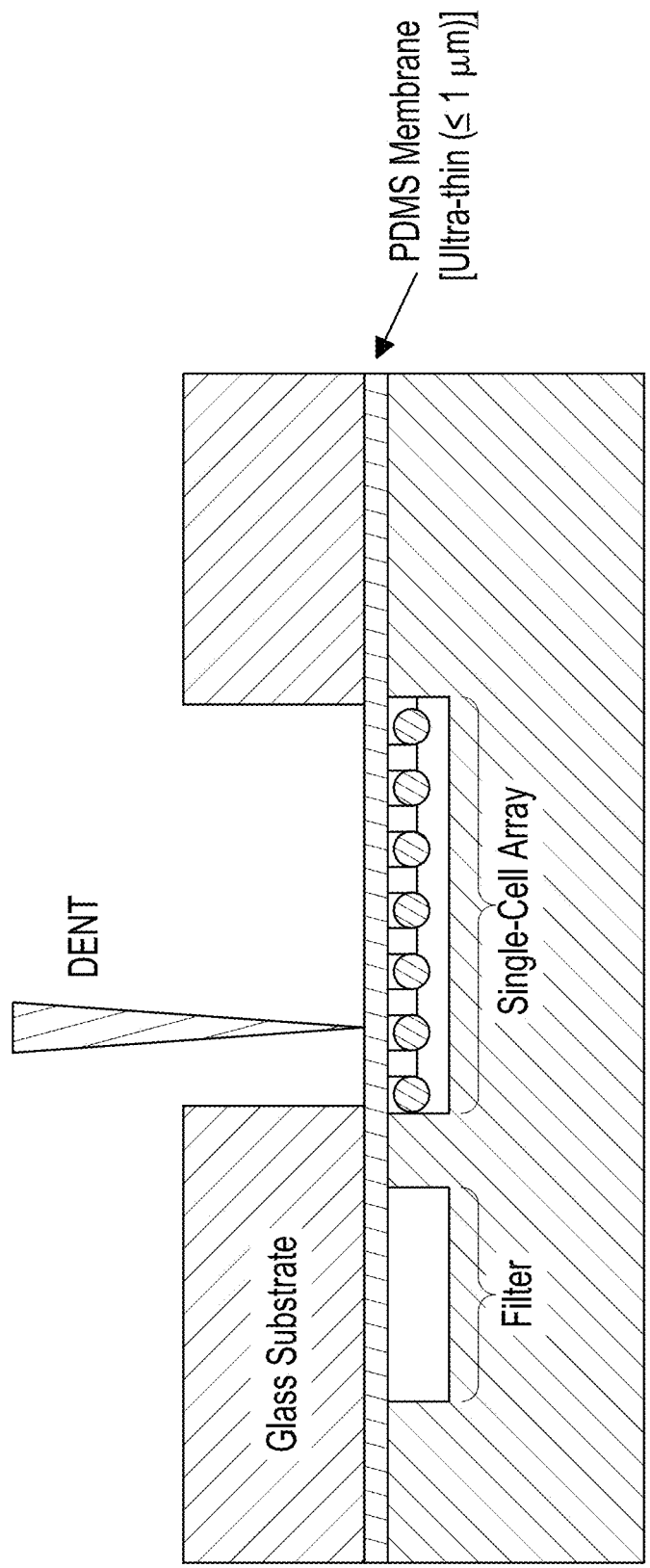
FIG. 14A schematically illustrates an external micromanipulator configured to extract mRNA from a single cell trapped in a cell trap of a trapping array.

Each individual cell trapped in the trapping array (e.g., as depicted in FIG. 13) can be subject to an analysis. The analysis can include extracting intra-cellular compounds, such as, for example mRNA. One method of performing single-cell analysis can include placing the microfluidic device encapsulated with a thin layer of polymer material (e.g., similar to the device depicted in FIGS. 5A and 5B) under microscope (e.g., an upright microscope) and on top of a motorized chip-holding stage. An external micro-manipulator (e.g., a DENT or an AFM probe) can be moved to a selected cell of interest as illustrated in FIG. 14A, followed by penetrating through the thin layer of polymer material and entering into a specific cell (e.g., through a cell wall) under the control of a micro motor, as illustrated in FIG. 14B. The interface between the probe and the layer of polymer material could be observed from deformation of the layer of polymer material under microscope. Once the external micro-manipulator is in contact with the layer of polymer material, the external micro-manipulator can be moved in short steps to penetrate through the layer of polymer material and enter into the cell. For example, a controller can be configured to apply short voltage pulses to a control motor configured to move the external micro-manipulator down in pulse steps, so that the external micromanipulator was able to penetrate through the layer of polymer material and enter into the cell.

Fabrication of the Modified AFM Probe

In various embodiments, the external micro-manipulator can comprise a modified atomic force microscope (AFM) probe. Scanning Electronic Microscopy (SEM) images of the modified AFM probe are shown in FIG. 14C. In one embodiment, the modified AFM probe was fabricated based on a commercially available conical, highly doped (resistivity 4 to 6 ohm-cm, k-4SN/m) silicon AFM probe available from Applied Nanotech, Inc., U.S. The fabrication process comprises growing a 20 nm thick layer of SiO2 on the AFM probe by conventional oxidation furnace. The $SiO_2$ layer served to electrically insulate the entire silicon probe including the cantilever. Then a 10 nm chromium adhesion layer followed by a 20 nm gold layer were deposited on top of the $SiO_2$ layer to serve as the outer electrode by Ion-beam sputtering. In the final step, the probe-end was polished by a flat $Si_3N_4$ wafer, so that the probe end was cut carefully, and the inner-doped silicon core was exposed. The exposed inner-doped silicon core can be configured to form the second electrode for dielectrophoresis (DEP).

In another embodiment, the modified AFM probe is a highly doped silicon probe coated with a 20 nm $SiO_2$ electrical insulation layer and a 10 nm/30 nm Cr/Au outer electrode, with its end cut so that the silicon core (inner electrode) is exposed.

Principle of Intra-Cellular Molecule Extraction Using a Modified AFM Probe

The modified AFM probe can be regarded as a dielectrophoretic nanotweezer (DENT). Application of an AC (alternating current) electric field between the inner (silicon core) and outer electrodes (Cr/Au nano-layer) of the AFM probe creates a large electric field gradient, resulting in a dielectrophoretic force strong enough to attract molecules (e.g. mRNAs, proteins, small molecules) to the probe-end. The DEP force is given by the equation $F_{DEP}=[(V\alpha)/2]\nabla|E|^2$, where V is the particle volume and a is the polarizability. In an embodiment, AC voltage of 1.5 $V_{pp}$ at 10 MHz was applied to the modified AFM prove-end. The modified AFM probe-end was removed from the cell after approximately 60-75 seconds and the AC field was turned off. In various embodiments, selective mRNA extraction can be achieved by decorating the probe with the oligonucleotide primers hybridizing to the target mRNA. After the AC electric field application, all the mRNAs move toward the probe-end, but only target mRNA molecules hybridize to the oligonucleotide primers. After hybridization, the probe is withdrawn from the cell and the AC field is tuned off.

mRNA obtained from each microspore may be used for genotyping. Optionally, the mRNA may be used to generate corresponding cDNAs. Genotyping may be done using any method known to one of ordinary skill in the art, including but not limited to sequence-based methods (genome-wide or targeted), exome capture, hybridization methods (liquid, array, solid support and the like), as well as amplification based methods, including but not limited to polymerase chain reaction (PCR, e.g., Taqman), molecular probes (e.g., molecular inversion probes).

Any relevant genetic marker or set of genetic markers can be used to genotype the microspores. This may include whole genome sequencing, southern by sequencing, a genome-wide marker set, a chromosome marker set, a trait marker set, imputation, or any combination thereof. Further, any suitable type of marker can be used, including Restriction Fragment Length Polymorphisms (RFLPs), Single Sequence Repeats (SSRs), Target Region Amplification Polymorphisms (TRAPs), Isozyme Electrophoresis, Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Single Nucleotide Polymorphisms (SNPs).

In the example target mRNA molecules can then be released as depicted in Panel (a) of FIG. 14B to perform qRT-PCR. The modified AFM probe can be configured to penetrate through the layer of polymer material and access another cell trapped in a different portion of the single cell trapping array during or after the contents of the specific cell are being analyzed.

Figure 15:
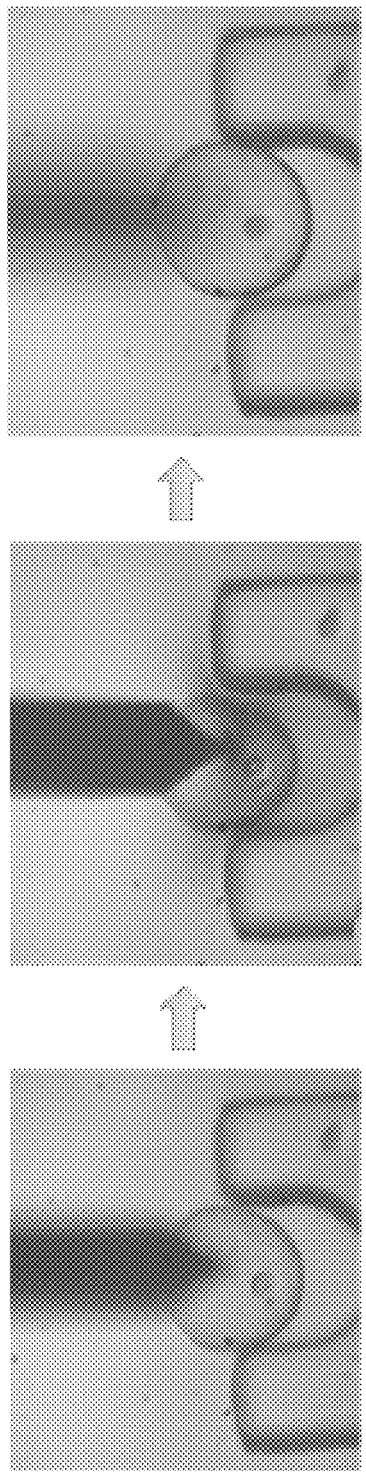
FIG. 15 illustrates bright-field microscopic images recording the procedure of mRNA extraction from a single-plant cell using DENT.

The microscopic images recording the procedure of single plant cell mRNA probing are shown in FIG. 15. The AFM probe was controlled to move to a target cell, penetrate through the thin layer of polymer material to enter into the cytoplasm, extract mRNA molecules out by DEP upon the application of AC field, and retract from the cell after mRNA probing.

The isolated mRNA molecules were then released from the probe-end into the PCR tubes, and went through qRT-PCR process to reveal the single-cellular expression levels of target genes. For plant tissue samples shipped from Kunia, two house-keeping genes, L01 and A02, were analysed. The analysis results of the L01 gene is shown in FIG. 16A and the analysis results of the A02 gene is shown in FIG. 16B. When an AC field of 1.9 Vpp, 10 Hz was used during the mRNA probing process, the amplifcation plot of extracted mRNA molecules from 3 different single plant cells are shown in FIGS. 16A and 16B. This is a proof of concept that mRNAs from plant cells can be successfully isolated by the proposed platform and there is obvious gene-expression heterogeneity among the cell population. Referring to FIG. 16A, curves 1602 and 1604 depict the analysis results for L01 templates and curves 1606, 1608 and 1610 show the analysis results for the L01 gene obtained from mRNA extracted from three different cells using a modified AFM probe. Referring to FIG. 16B, curves 1612 and 1614 depict the analysis results for A02 templates and curves 1616, 1618 and 1620 show the analysis results for the A02 gene obtained from mRNA extracted from three different cells using a modified AFM probe.

Figures 17A, 17B, 17C, 17D:
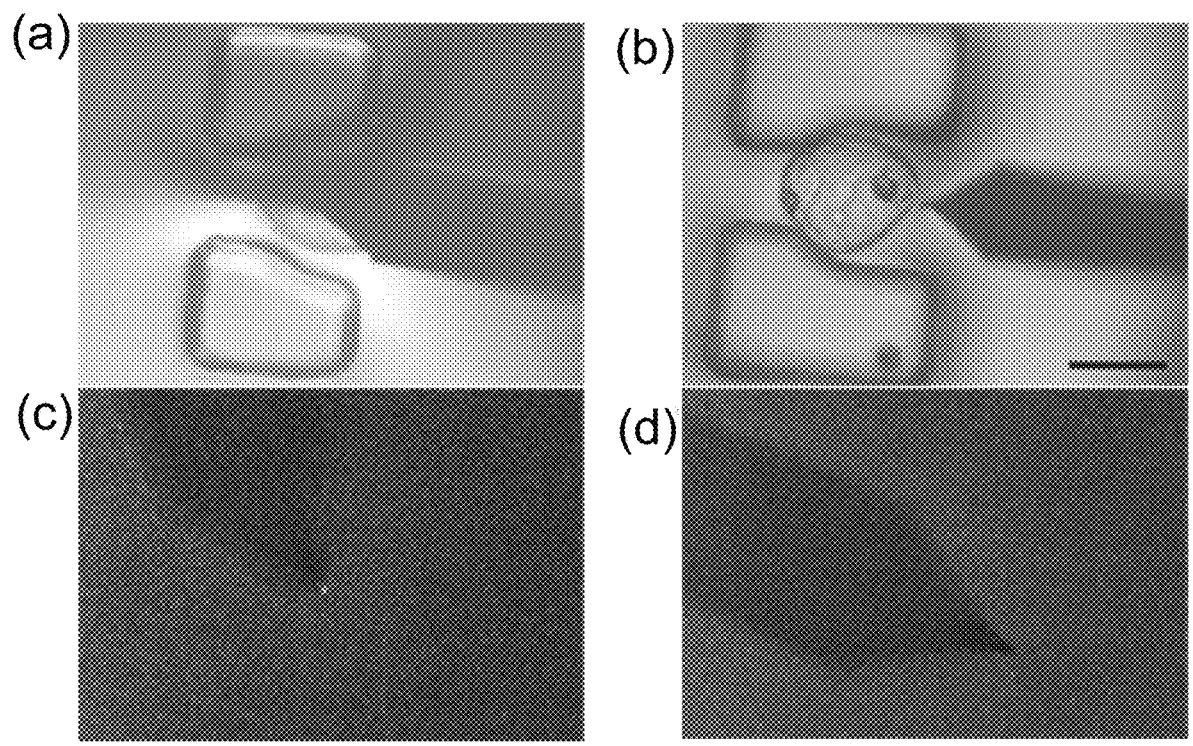
FIG. 17 is a comparison of the probed-out molecules when DENT penetrated into the cytoplasm or the surrounding media. Panel (a) illustrates DENT penetrated into a target plant cell. Panel (b) illustrates DENT penetrated into the cell's surrounding media. Fluorescent images of the probe-end whether a probe penetrated into a cell stained by Calcein AM or the surrounding media are shown in Panel (c) and Panel (d) respectively. The qRT-PCR amplification plots and the melting curves of molecules released from the probe that penetrated into the cytoplasm are shown in Panel (e) and Panel (f) respectively. The qRT-PCR amplification plots and the melting curves of molecules released from the probe that penetrated into the surrounding media are shown in are shown in Panel (g) and Panel (h) respectively.
Figures 17E, 17F, 17G, 17H:
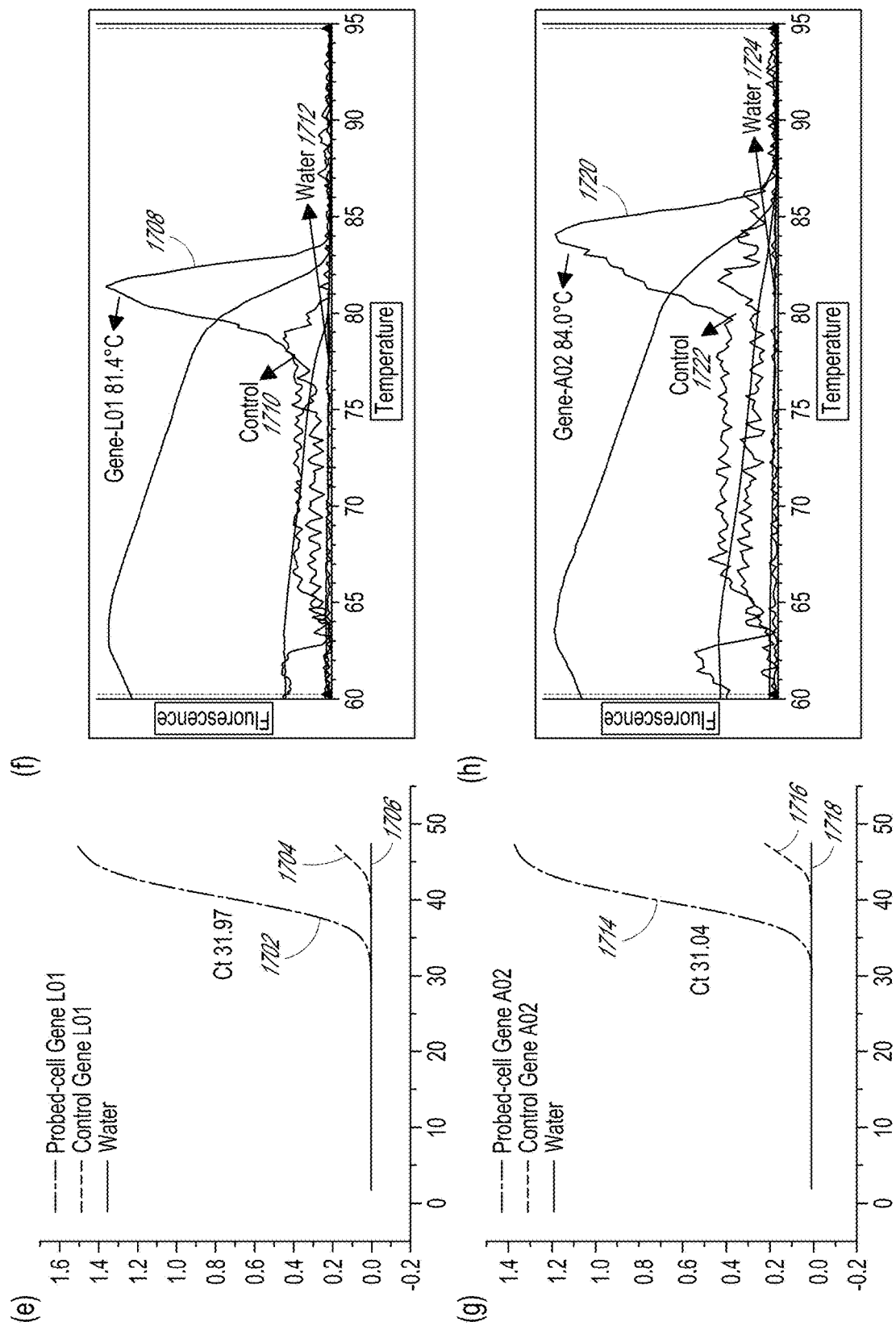

To verify that the above qRT-PCR results were indeed from plant cell cytoplasm and not from the surrounding media, experiments were carried out to compare the results between probing into a plant cell and probing into the cell's surrounding culture media. The results from these experiments are depicted in FIG. 17. For cells were stained by Calcein AM, fluorescent molecules attached to the AFM probe-end only when the AFM prove penetrated into the cell, while when the AFM probe dipped into the media it did not have any fluorescent attached molecules attached to the AFM probe-end as depicted in Panels (c) and (d) of FIG. 17. Referring to panel (e) of FIG. 17 curve 1702 depicts the analysis for the L01 gene, curve 1704 depicts the analysis for a control L01 gene and curve 1706 for water (representing the surrounding medium). Referring to panel (f) of FIG. 17 curve 1708 depicts the analysis for the L01 gene, curve 1710 depicts the analysis for a control L01 gene and curve 1712 for water (representing the surrounding medium). Referring to panel (g) of FIG. 17 curve 1714 depicts the analysis for the A02 gene, curve 1716 depicts the analysis for a control A02 gene and curve 1718 for water (representing the surrounding medium). Referring to panel (h) of FIG. 17 curve 1720 depicts the analysis for the A02 gene, curve 1722 depicts the analysis for a control A02 gene and curve 1724 for water (representing the surrounding medium).

Furthermore, when comparing the qRT-PCR amplification plots, only the molecules released from the probe that penetrated into the cytoplasm had true amplifications for both gene L01 and gene A02 as depicted in Panels (e) and (g) of FIG. 17, with specific melting curves as depicted in Panels (f) and (h) of FIG. 17. The above results verify that the qRT-PCR amplification plots of mRNA molecules released from the DENT probe after cell penetration were meaningful results representing the single-cell gene-expression levels, instead of false positive readings from the surrounding media.

Figure 18B:
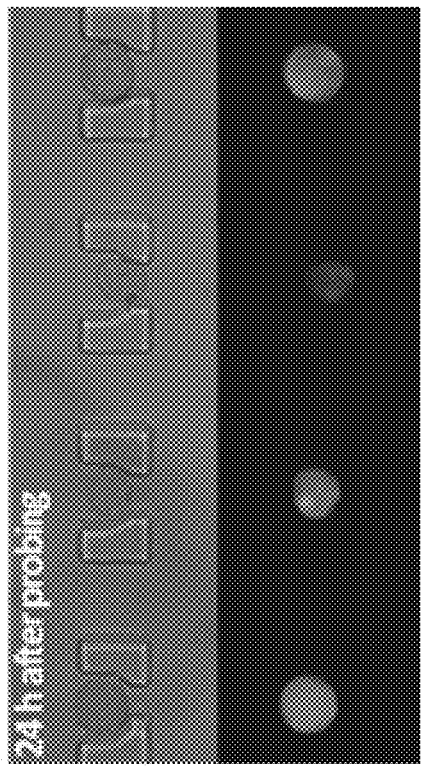
FIGS. 18A and 18B illustrate viability analysis of probed plant cells using Calcein AM staining. Bright-field and fluorescence images of plant cells cultured on chip 1 hour after mRNA extraction using DENT is shown in FIG. 18A and 24 hours after mRNA extraction using DENT is shown in FIG. 18B.
Figure 18A:
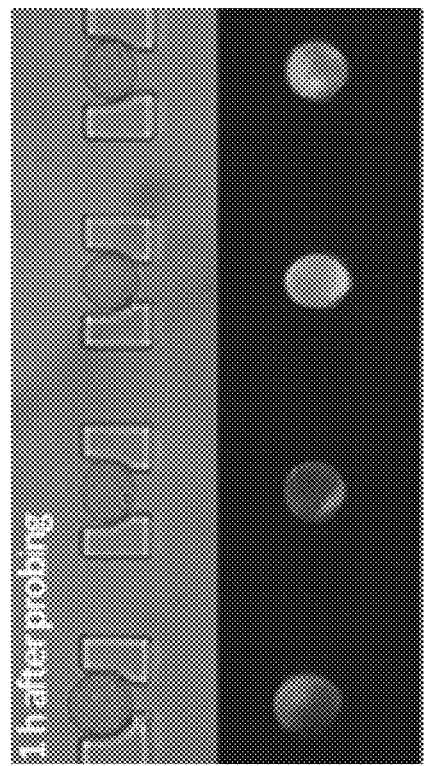

The viability of cells after probing was also analyzed. Cells were probed at 1.9 Vpp, 10 Hz, and cultured with in the microfluidic chip using C1 media shipped from Johnston, Pioneer. They were stained with Calcein AM 1 hour after the mRNA was extracted by the AFM probe, and cultured on-chip for 24 hours. 1 hour after the mRNA was extracted by the AFM probe, most of the cells were viable with impact morphology and strong green fluorescence as shown in FIG. 18A. After 24 hours of on-chip culturing, cells shrunk and some exhibited plasmolysis as shown in FIG. 18B, with an average viability around 50%.

What is claimed is:

1. A micro fluidic device configured to non-destructively obtaining a genotype
of a plant cell, the device comprising:
an inlet configured to receive a plant cell sample comprising a plurality of plant cells;
a micro fluidic channel in fluid communication with the inlet;
an obstacle array configured to focus the plant cell sample to a sidewall of the microfluidic channel;
an electrode array configured to separate a first constituent from the focused plant cell sample by deflecting the first constituent of the focused plant cell sample towards a central portion of the micro fluidic channel;
a single-cell trapping array located downstream from the electrode array, the single-cell trapping array comprising a microwell array configured to trap a single plant cell from the first constituent of the plant cell sample in a microwell of the microwell array;
a polymer membrane encapsulating the single-cell trapping array; and
an external micro-manipulating instrument configured to pierce the polymer membrane and penetrate a respective cell wall of the trapped single plant cell to extract mRNA from the trapped single plant cell using a dielectrophoresis (DEP) force under an alternating current (AC) field applied to the external micro-manipulating instrument.

2. The device of claim 1, wherein the external micro-manipulating instrument comprises a probe tip of an Atomic Force Microscope (AFM).

3. The device of claim 1, wherein the external micro-manipulating instrument comprises a dielectrophoretic nano tweezer (DENT).

4. The device of claim 1, wherein the polymer membrane has a thickness less than 5 micron.

5. The device of claim 1, wherein the polymer membrane is configured to be resealable after removal of the external micro-manipulating instrument.

6. The device of claim 1, wherein the plant cell sample is a plant selected from maize or canola.

7. The device of claim 1, wherein the plant cell sample is a microspore having a preselected genotype wherein the preselection is based upon one allele or multiple alleles.

8. The device of claim 1, wherein the plant cell sample is a microspore having a preselected genotype wherein the preselection is based upon one allele or multiple alleles.

9. The device of claim 1, wherein the plurality of plant cells are selected from the group consisting of microspores and protoplasts.

10. The device of claim 9, wherein the plurality of plant cells are tetrad mlcrospores.

11. The device of claim 1, further comprising an analysis chamber configured to analyze mRNA extracted from the trapped single plant cell to determine gene expression patterns of the plant cell.

12. The device of claim 1, further comprising an analysis chamber configured to determine the genotype of the trapped single plant cell from cDNA obtained from mRNA extracted from the trapped single plant cell.

* * * * *